(12) United States Patent
Shuros et al.

(10) Patent No.: US 8,521,278 B2
(45) Date of Patent: Aug. 27, 2013

(54) SMART DELAY FOR INTERMITTENT STRESS THERAPY

(75) Inventors: Allan C. Shuros, St. Paul, MN (US); Shantha Arcot-Krishnamurthy, Vadnais Heights, MN (US); Robert Shipley, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 349 days.

(21) Appl. No.: 12/436,497

(22) Filed: May 6, 2009

(65) Prior Publication Data

US 2009/0281591 A1    Nov. 12, 2009

Related U.S. Application Data

(60) Provisional application No. 61/051,529, filed on May 8, 2008.

(51) Int. Cl.
*A61N 1/00* (2006.01)

(52) U.S. Cl.
USPC .......................................................... 607/9

(58) Field of Classification Search
USPC .......................................................... 607/9
See application file for complete search history.

(56) References Cited

U.S. PATENT DOCUMENTS

| | | |
|---|---|---|
| 3,995,623 A | 12/1976 | Blake et al. |
| 4,354,497 A | 10/1982 | Kahn |
| 4,386,610 A | 6/1983 | Leckrone |
| 4,401,119 A | 8/1983 | Herpers |
| 4,432,362 A | 2/1984 | Leckrone et al. |
| 4,485,813 A | 12/1984 | Anderson et al. |
| 4,674,518 A | 6/1987 | Salo |
| 4,686,987 A | 8/1987 | Salo et al. |
| 4,719,921 A | 1/1988 | Chirife |

(Continued)

FOREIGN PATENT DOCUMENTS

| | | |
|---|---|---|
| EP | 0474958 A2 | 3/1992 |
| EP | 0545628 A2 | 6/1993 |

(Continued)

OTHER PUBLICATIONS

"U.S. Appl. No. 09/075,278, Advisory Action mailed Jan. 28, 2000", 2 pgs.

(Continued)

*Primary Examiner* — Christopher D Koharski
*Assistant Examiner* — Philip Edwards
(74) *Attorney, Agent, or Firm* — Schwegman Lundberg & Woessner, P.A.

(57) ABSTRACT

A pacing system delivers cardiac protection pacing to protect the heart from injuries. The pacing system receives a set of inputs and calculates parameters for delivering optimized cardiac protection pacing tailored for different stress levels. The system automatically adjusts heart rate to optimize cardiac protection pacing in a closed-loop system. In one embodiment, a method for delivering pacing pulses for cardiac protection is provided. Intrinsic atrioventricular (AV) intervals are sensed. The intrinsic AV interval and a predetermined equation relating the AV interval to an optimal AV delay are used to provide a maximum positive rate of left ventricular pressure change during systole. An AV delay is calculated using a predetermined percentage of the optimal AV delay to deliver ventricular pacing pulses to provide a desired level of stress for cardiac protective pacing therapy (CPPT) to provide a cardiac conditioning therapy to improve autonomic balance.

22 Claims, 12 Drawing Sheets

(56) References Cited

U.S. PATENT DOCUMENTS

| | | | |
|---|---|---|---|
| 4,872,459 A | 10/1989 | Pless et al. | |
| 4,880,005 A | 11/1989 | Pless et al. | |
| 4,922,907 A | 5/1990 | Hedin et al. | |
| 4,928,688 A | 5/1990 | Mower | |
| 4,945,909 A | 8/1990 | Fearnot et al. | |
| 5,014,698 A | 5/1991 | Cohen | |
| 5,083,563 A | 1/1992 | Collins | |
| 5,101,824 A | 4/1992 | Lekholm | |
| 5,129,394 A | 7/1992 | Mehra | |
| 5,139,020 A | 8/1992 | Koestner et al. | |
| 5,156,149 A | 10/1992 | Hudrlik | |
| 5,158,079 A | 10/1992 | Adams et al. | |
| 5,161,540 A | 11/1992 | Mueller | |
| 5,163,429 A | 11/1992 | Cohen | |
| 5,168,869 A | 12/1992 | Chirife | |
| 5,174,289 A | 12/1992 | Cohen | |
| 5,179,949 A | 1/1993 | Chirife | |
| 5,233,985 A | 8/1993 | Hudrlik | |
| 5,267,560 A | 12/1993 | Cohen | |
| 5,318,595 A | 6/1994 | Ferek-Petric et al. | |
| 5,324,326 A | 6/1994 | Lubin | |
| 5,330,511 A | 7/1994 | Boute | |
| 5,331,768 A | 7/1994 | Takeuchi | |
| 5,334,222 A | 8/1994 | Salo et al. | |
| 5,370,665 A | 12/1994 | Hudrlik | |
| 5,372,607 A | 12/1994 | Stone et al. | |
| 5,464,434 A | 11/1995 | Alt | |
| 5,514,161 A | 5/1996 | Limousin | |
| 5,514,163 A | 5/1996 | Markowitz et al. | |
| 5,527,347 A | 6/1996 | Shelton et al. | |
| 5,534,016 A | 7/1996 | Boute | |
| 5,549,650 A | 8/1996 | Bornzin et al. | |
| 5,554,177 A | 9/1996 | Kieval et al. | |
| 5,584,867 A | 12/1996 | Limousin et al. | |
| 5,584,868 A | 12/1996 | Salo et al. | |
| 5,609,612 A | 3/1997 | Plicchi et al. | |
| 5,609,613 A | 3/1997 | Woodson et al. | |
| 5,626,620 A | 5/1997 | Kieval et al. | |
| 5,626,621 A | 5/1997 | Skoglund et al. | |
| 5,626,623 A | 5/1997 | Kieval et al. | |
| 5,628,777 A | 5/1997 | Moberg et al. | |
| 5,674,259 A | 10/1997 | Gray | |
| 5,683,429 A | 11/1997 | Mehra | |
| 5,690,689 A | 11/1997 | Sholder | |
| 5,700,283 A | 12/1997 | Salo | |
| 5,713,930 A | 2/1998 | van der Veen et al. | |
| 5,716,383 A | 2/1998 | Kieval et al. | |
| 5,728,140 A | 3/1998 | Salo et al. | |
| 5,749,906 A | 5/1998 | Kieval et al. | |
| 5,755,739 A | 5/1998 | Sun et al. | |
| 5,755,766 A | 5/1998 | Chastain et al. | |
| 5,797,970 A | 8/1998 | Pouvreau | |
| 5,800,471 A | 9/1998 | Baumann | |
| 5,824,019 A | 10/1998 | Rueter et al. | |
| 5,919,209 A | 7/1999 | Schouten | |
| 5,935,160 A | 8/1999 | Auricchio et al. | |
| 6,038,483 A | 3/2000 | KenKnight et al. | |
| 6,044,298 A | 3/2000 | Salo et al. | |
| 6,058,329 A | 5/2000 | Salo et al. | |
| 6,070,101 A * | 5/2000 | Struble et al. | 607/9 |
| 6,108,577 A | 8/2000 | Benser | |
| 6,112,117 A | 8/2000 | KenKnight et al. | |
| 6,128,526 A | 10/2000 | Stadler et al. | |
| 6,136,021 A | 10/2000 | Tockman et al. | |
| 6,144,880 A | 11/2000 | Ding et al. | |
| 6,151,524 A | 11/2000 | Krig et al. | |
| 6,152,955 A | 11/2000 | KenKnight et al. | |
| 6,198,952 B1 | 3/2001 | Miesel | |
| 6,208,901 B1 | 3/2001 | Hartung | |
| 6,223,082 B1 | 4/2001 | Bakels et al. | |
| 6,273,856 B1 | 8/2001 | Sun et al. | |
| 6,280,389 B1 | 8/2001 | Ding et al. | |
| 6,304,777 B1 | 10/2001 | Ben-Haim et al. | |
| 6,309,350 B1 | 10/2001 | VanTassel et al. | |
| 6,311,089 B1 | 10/2001 | Mann et al. | |
| 6,314,322 B1 | 11/2001 | Rosenberg | |
| 6,351,673 B1 | 2/2002 | Ding et al. | |
| 6,360,127 B1 | 3/2002 | Ding et al. | |
| 6,398,738 B1 | 6/2002 | Millar | |
| 6,418,346 B1 | 7/2002 | Nelson et al. | |
| 6,430,439 B1 | 8/2002 | Wentkowski et al. | |
| 6,438,421 B1 | 8/2002 | Stahmann et al. | |
| 6,449,510 B1 | 9/2002 | Albers et al. | |
| 6,480,742 B2 | 11/2002 | Stahmann et al. | |
| 6,507,756 B1 | 1/2003 | Heynen et al. | |
| 6,512,952 B2 | 1/2003 | Stahmann et al. | |
| 6,522,921 B2 | 2/2003 | Stahmann et al. | |
| 6,522,923 B1 | 2/2003 | Turcott | |
| 6,542,775 B2 | 4/2003 | Ding et al. | |
| 6,553,258 B2 | 4/2003 | Stahmann et al. | |
| 6,597,951 B2 | 7/2003 | Kramer et al. | |
| 6,654,637 B2 | 11/2003 | Rouw et al. | |
| 6,666,826 B2 | 12/2003 | Salo et al. | |
| 6,684,103 B2 | 1/2004 | Ding et al. | |
| 6,754,532 B1 | 6/2004 | Ferek-Petric | |
| 6,795,732 B2 | 9/2004 | Stadler et al. | |
| 6,804,555 B2 * | 10/2004 | Warkentin | 607/9 |
| 6,832,113 B2 | 12/2004 | Belalcazar | |
| 6,856,836 B2 | 2/2005 | Ding et al. | |
| 6,859,665 B2 | 2/2005 | Ding et al. | |
| 6,885,890 B2 | 4/2005 | Spinelli et al. | |
| 6,892,095 B2 | 5/2005 | Salo | |
| 6,915,164 B2 | 7/2005 | Bradley et al. | |
| 6,937,901 B2 | 8/2005 | Zhu et al. | |
| 6,970,742 B2 | 11/2005 | Mann et al. | |
| 7,013,176 B2 | 3/2006 | Ding et al. | |
| 7,092,759 B2 | 8/2006 | Nehls et al. | |
| 7,103,410 B2 * | 9/2006 | Kramer et al. | 607/9 |
| 7,110,817 B2 | 9/2006 | Yu et al. | |
| 7,158,830 B2 | 1/2007 | Yu et al. | |
| 7,167,743 B2 | 1/2007 | Heruth et al. | |
| 7,184,835 B2 | 2/2007 | Kramer et al. | |
| 7,206,634 B2 | 4/2007 | Ding et al. | |
| 7,215,997 B2 | 5/2007 | Yu et al. | |
| 7,231,248 B2 | 6/2007 | Kramer et al. | |
| 7,248,925 B2 * | 7/2007 | Bruhns et al. | 607/25 |
| 7,310,554 B2 * | 12/2007 | Kramer et al. | 607/9 |
| 7,313,440 B2 | 12/2007 | Miesel | |
| 7,395,113 B2 | 7/2008 | Heruth et al. | |
| 7,529,585 B2 | 5/2009 | Yu et al. | |
| 7,542,803 B2 | 6/2009 | Heruth et al. | |
| 7,856,270 B2 | 12/2010 | Ding et al. | |
| 7,974,695 B2 | 7/2011 | Yu et al. | |
| 8,032,214 B2 | 10/2011 | Yu et al. | |
| 8,103,345 B2 | 1/2012 | Ding et al. | |
| 2001/0047194 A1 | 11/2001 | Thompson et al. | |
| 2002/0002389 A1 | 1/2002 | Bradley et al. | |
| 2002/0123769 A1 | 9/2002 | Panken et al. | |
| 2002/0143264 A1 | 10/2002 | Ding et al. | |
| 2002/0151938 A1 | 10/2002 | Corbucci | |
| 2002/0183795 A1 | 12/2002 | Rouw et al. | |
| 2003/0078628 A1 | 4/2003 | Holmstrom et al. | |
| 2003/0097158 A1 | 5/2003 | Belalcazar | |
| 2003/0105496 A1 | 6/2003 | Yu et al. | |
| 2003/0125774 A1 | 7/2003 | Salo | |
| 2003/0130581 A1 | 7/2003 | Salo et al. | |
| 2003/0144702 A1 | 7/2003 | Yu et al. | |
| 2003/0144703 A1 | 7/2003 | Yu et al. | |
| 2004/0015081 A1 | 1/2004 | Kramer et al. | |
| 2004/0019365 A1 | 1/2004 | Ding et al. | |
| 2004/0078059 A1 | 4/2004 | Ding et al. | |
| 2004/0078060 A1 | 4/2004 | Ding et al. | |
| 2004/0147966 A1 | 7/2004 | Ding et al. | |
| 2004/0158290 A1 | 8/2004 | Girouard | |
| 2004/0193223 A1 | 9/2004 | Kramer et al. | |
| 2005/0038477 A1 | 2/2005 | Kramer et al. | |
| 2005/0102002 A1 | 5/2005 | Salo et al. | |
| 2005/0131472 A1 | 6/2005 | Ding et al. | |
| 2005/0137630 A1 | 6/2005 | Ding et al. | |
| 2005/0137631 A1 | 6/2005 | Yu et al. | |
| 2005/0137632 A1 | 6/2005 | Ding et al. | |
| 2006/0149326 A1 * | 7/2006 | Prinzen et al. | 607/17 |
| 2006/0253156 A1 | 11/2006 | Pastore et al. | |
| 2006/0276847 A1 | 12/2006 | Yu et al. | |

| | | | |
|---|---|---|---|
| 2007/0135854 | A1 | 6/2007 | Kramer et al. |
| 2007/0162081 | A1 | 7/2007 | Yu et al. |
| 2007/0179546 | A1 | 8/2007 | Yu et al. |
| 2007/0208386 | A1 | 9/2007 | Kramer et al. |
| 2009/0198299 | A1 | 8/2009 | Yu et al. |
| 2011/0071588 | A1 | 3/2011 | Ding et al. |

FOREIGN PATENT DOCUMENTS

| | | |
|---|---|---|
| EP | 0970721 A2 | 1/2000 |
| EP | 1070516 A2 | 1/2001 |
| JP | 07-506525 | 7/1995 |
| JP | 10-504753 | 5/1998 |
| JP | 2002-514478 | 5/2002 |
| JP | 2006511312 A | 4/2006 |
| JP | 2006515796 A | 6/2006 |
| WO | WO-99/10042 A1 | 3/1999 |
| WO | WO-99/58191 A1 | 11/1999 |
| WO | WO-01/76689 A2 | 10/2001 |
| WO | WO-02/087694 A1 | 11/2002 |
| WO | WO-2004/011088 A1 | 2/2004 |
| WO | WO-2004/069333 A2 | 8/2004 |
| WO | WO-2005/046788 A2 | 5/2005 |
| WO | WO-2006/037108 A1 | 4/2006 |
| WO | WO-2006/115659 A1 | 11/2006 |
| WO | WO-2009/151516 A1 | 12/2009 |

OTHER PUBLICATIONS

"U.S. Appl. No. 09/075,278, Advisory Action mailed Dec. 2, 1999", 1 pg.

"U.S. Appl. No. 09/075,278, Amendment Under 37 CFR §1.116 filed Jan. 28, 2000", 2 pgs.

"U.S. Appl. No. 09/075,278, Amendment Under 37 CFR §1.116 filed Feb. 11, 2000", 7 pgs.

"U.S. Appl. No. 09/075,278, Final Office Action mailed Sep. 17, 1999", 9 pgs.

"U.S. Appl. No. 09/075,278, Non-Final Office Action mailed Apr. 12, 1999", 10 pgs.

"U.S. Appl. No. 09/075,278, Notice of Allowance mailed Feb. 14, 2000", 4 pgs.

"U.S. Appl. No. 09/075,278, Preliminary Amendment filed Nov. 16, 1998", 8 pgs.

"U.S. Appl. No. 09/075,278, Response filed Aug. 12, 1999 to Non-Final Office Action mailed Apr. 12, 1999", 16 pgs.

"U.S. Appl. No. 09/075,278, Response filed Nov. 17, 1999 to Final Office Action mailed Sep.17, 1999", 4 pgs.

"U.S. Appl. No. 09/075,278, Response filed Dec. 17, 1999 to Final Office Action mailed Sep. 17, 1999 and Advisory Action mailed Dec. 2, 1999", 4 pgs.

"U.S. Appl. No. 09/492,911, Amendment Under 37 C.F.R. §1.312(a) filed Oct. 16, 2001", 3 pgs.

"U.S. Appl. No. 09/492,911, Non-Final Office Action mailed Oct. 27, 2000", 6 pgs.

"U.S. Appl. No. 09/492,911, Notice of Allowance Mar. 20, 2001", 8 pgs.

"U.S. Appl. No. 09/492,911, Notice of Allowance mailed Jul. 16, 2001", 3 pgs.

"U.S. Appl. No. 09/492,911, Preliminary Amendment filed Jan. 20, 2000", 4 pgs.

"U.S. Appl. No. 09/492,911, Response filed Jan. 29, 2001 to Non-Final Office Action mailed Oct. 27, 2000", 7 pgs.

"U.S. Appl. No. 09/492,911, Response filed Sep. 14, 2000 to Restriction Requirement mailed Aug. 15, 2000", 4 pgs.

"U.S. Appl. No. 09/492,911, Restriction Requirement mailed Aug. 15, 2000", 4 pgs.

"U.S. Appl. No. 09/661,608, Non-Final Office Action mailed Feb. 28, 2001", 6 pgs.

"U.S. Appl. No. 09/661,608, Notice of Allowance mailed Aug. 27, 2001", 3 pgs.

"U.S. Appl. No. 09/661,608, Preliminary Amendment filed Sep. 14, 2000", 4 pgs.

"U.S. Appl. No. 09/661,608, Response filed Jun. 28, 2001 to Non-Final Office Action mailed Feb. 28, 2001", 11 pgs.

"U.S. Appl. No. 09/661,608, Supplemental Amendment filed Aug. 24, 2001", 4 pgs.

"U.S. Appl. No. 09/661,608, Supplemental Notice of Allowance mailed Oct. 18, 2001", 2 pgs.

"U.S. Appl. No. 09/962,852, Notice of Allowance mailed Oct. 10, 2007", 6 pgs.

"U.S. Appl. No. 09/962,852, Advisory Action mailed Feb. 1, 2007", 3 pgs.

"U.S. Appl. No. 09/962,852, Final Office Action mailed Sep. 22, 2004", 14 pgs.

"U.S. Appl. No. 09/962,852, Final Office Action mailed Oct. 13, 2005", 12 pgs.

"U.S. Appl. No. 09/962,852, Final Office Action mailed Oct. 18, 2006", 14 pgs.

"U.S. Appl. No. 09/962,852, Non-Final Office Action filed Mar. 20, 2007", 11 pgs.

"U.S. Appl. No. 09/962,852, Non-Final Office Action mailed Mar. 8, 2006", 13 pgs.

"U.S. Appl. No. 09/962,852, Non-Final Office Action mailed Mar. 11, 2004", 10 pgs.

"U.S. Appl. No. 09/962,852, Non-Final Office Action mailed Mar. 22, 2005", 10 pgs.

"U.S. Appl. No. 09/962,852, Response filed Jan. 13, 2006 to Final Office Action mailed Oct. 13, 2005", 8 pgs.

"U.S. Appl. No. 09/962,852, Response filed Jan. 18, 2007 to Final Office Action mailed Oct. 18, 2006", 9 pgs.

"U.S. Appl. No. 09/962,852, Response filed Jan. 24, 2005 to Final Office Action mailed Sep. 22, 2004", 9 pgs.

"U.S. Appl. No. 09/962,852, Response filed Jun. 14, 2004 to Non-Final Office Action mailed Mar. 11, 2004", 8 pgs.

"U.S. Appl. No. 09/962,852, Response filed Jul. 20, 2007 to Non-Final Office Action filed Mar. 20, 2007", 9 pgs.

"U.S. Appl. No. 09/962,852, Response filed Jul. 21, 2005 to Non-Final Office Action mailed Mar. 22, 2005", 9 pgs.

"U.S. Appl. No. 09/962,852, Response filed Aug. 8, 2006 to Non-Final Office Action mailed Mar. 8, 2006", 9 pgs.

"U.S. Appl. No. 10/008,830, Non-Final Office Action mailed May 23, 2002", 10 pgs.

"U.S. Appl. No. 10/008,830, Notice of Allowance mailed Oct. 30, 2002", 8 pgs.

"U.S. Appl. No. 10/008,830, Preliminary Amendment filed Dec. 7, 2001", 2 pgs.

"U.S. Appl. No. 10/008,830, Response filed Aug. 23, 2002 to Non-Final Office Action mailed May 23, 2002", 13 pgs.

"U.S. Appl. No. 10/008,830, Supplemental Preliminary Amendment filed Feb. 7, 2002", 4 pgs.

"U.S. Appl. No. 10/206,131, Non-Final Office Action mailed Feb. 3, 2006", 5 pgs.

"U.S. Appl. No. 10/206,131, Non-Final Office Action mailed Jul. 7, 2006", 7 pgs.

"U.S. Appl. No. 10/206,131, Non-Final Office Action mailed Oct. 6, 2005", 5 pgs.

"U.S. Appl. No. 10/206,131, Notice of Allowance mailed Dec. 6, 2006", 4 pgs.

"U.S. Appl. No. 10/206,131, Response filed Jan. 5, 2006 to Non-Final Office Action mailed Oct. 6, 2005", 8 pgs.

"U.S. Appl. No. 10/206,131, Response filed May 3, 2006 to Non-Final Office Action mailed Feb. 3, 2006", 8 pgs.

"U.S. Appl. No. 10/206,131, Response filed Oct. 10, 2006 to Non-Final Office Action mailed Jul. 7, 2006", 11 pgs.

"U.S. Appl. No. 10/243,811, Non-Final Office Action mailed Mar. 20, 2003", 5 pgs.

"U.S. Appl. No. 10/243,811, Notice of Allowance mailed Sep. 3, 2003", 5 pgs.

"U.S. Appl. No. 10/243,811, Response filed Feb. 14, 2003 to Restriction Requirement mailed Jan. 14, 2003", 1 pg.

"U.S. Appl. No. 10/243,811, Response filed Jun. 16, 2003 to Non-Final Office Action mailed Mar. 20, 2003", 10 pgs.

"U.S. Appl. No. 10/243,811, Restriction Requirement mailed Jan. 14, 2003", 4 pgs.

"U.S. Appl. No. 10/314,899, Advisory Action mailed Jul. 11, 2006", 3 pgs.

"U.S. Appl. No. 10/314,899, Final Office Action mailed Apr. 24, 2006", 8 pgs.

"U.S. Appl. No. 10/314,899, Non-Final Office Action mailed Dec. 15, 2005", 11 pgs.

"U.S. Appl. No. 10/314,899, Notice of Allowance mailed Aug. 23, 2006", 6 pgs.

"U.S. Appl. No. 10/314,899, Response filed Mar. 15, 2006 to Non-Final Office Action mailed Dec. 15, 2005", 11 pgs.

"U.S. Appl. No. 10/314,899, Response filed Jun. 23, 2006 to Final Office Action mailed Apr. 24, 2006", 10 pgs.

"U.S. Appl. No. 10/314,910, Non-Final Office Action mailed Dec. 16, 2005", 13 pgs.

"U.S. Appl. No. 10/314,910, Response filed Mar. 16, 2006 to Non Final Office Action mailed Dec. 16, 2005", 14 pgs.

"U.S. Appl. No. 10/314,910, Notice of Allowance mailed May 5, 2006", 8 pgs.

"U.S. Appl. No. 10/352,780, Notice of Allowance mailed Aug. 16, 2005", 6 pgs.

"U.S. Appl. No. 10/615,201, Non-Final Office Action mailed Jun. 3, 2004", 6 pgs.

"U.S. Appl. No. 10/615,201, Notice of Allowance mailed Oct. 4, 2004", 7 pgs.

"U.S. Appl. No. 10/615,201, Response filed Aug. 31, 2004 to Non-Final Office Action mailed Jun. 3, 2004", 9 pgs.

"U.S. Appl. No. 10/615,202, Non-Final Office Action mailed Jun. 14, 2004", 4 pgs.

"U.S. Appl. No. 10/615,202, Notice of Allowance mailed Oct. 4, 2004", 7 pgs.

"U.S. Appl. No. 10/615,202, Response filed Aug. 31, 2004 to Non-Final Office Action mailed Jun. 14, 2004", 9 pgs.

"U.S. Appl. No. 10/735,267, Notice of Allowance mailed Jun. 9, 2006", 6 pgs.

"U.S. Appl. No. 11/049,181, Restriction Requirement mailed Mar. 14, 2008", 7 pgs.

"U.S. Appl. No. 11/049,181, Response filed Nov. 14, 2008 to Non-Final Office Action mailed Aug. 14, 2008", 8 pgs.

"U.S. Appl. No. 11/049,181, Final Office Action mailed Feb. 5, 2009", 5 pgs.

"U.S. Appl. No. 11/049,181, Advisory Action mailed Apr. 13, 2009", 3 pgs.

"U.S. Appl. No. 11/049,181, Non-Final Office Action mailed Aug. 14, 2008", 7 pgs.

"U.S. Appl. No. 11/049,181, Examiner Interview Summary mailed Oct. 21, 2009", 3 pgs.

"U.S. Appl. No. 11/049,181, Final Office Action mailed Feb. 4, 2010", 7 pgs.

"U.S. Appl. No. 11/049,181, Non-Final Office Action mailed Jul. 23, 2009", 6 pgs.

"U.S. Appl. No. 11/049,181, Response filed Apr. 6, 2009 to Final Office Action mailed Feb. 5, 2009", 7 pgs.

"U.S. Appl. No. 11/049,181, Response filed Apr. 14, 2008 to Restriction Requirement mailed Mar. 14, 2008", 6 pgs.

"U.S. Appl. No. 11/049,181, Response filed May 5, 2009 to Final Office Action mailed Feb. 5, 2009 and Advisory Action mailed Apr. 13, 2009", 7 pgs.

"U.S. Appl. No. 11/049,181, Response filed Oct. 23 2009 to Non Final Office Action mailed Jul. 23, 2009", 8 pgs.

"U.S. Appl. No. 11/463,176, Notice of Allowance mailed Dec. 24, 2008", 4 pgs.

"U.S. Appl. No. 11/463,176, Non-Final Office Action mailed Aug. 14, 2008", 6 pgs.

"U.S. Appl. No. 11/463,176, Response filed Nov. 14, 2008 to Non-Final Office Action mailed Aug. 14, 2008", 11 pgs.

"U.S. Appl. No. 11/674,773, Non-Final Office Action mailed Oct. 21, 2009", 7 pgs.

"European Application Serial No. 02766357.4, Communication mailed Dec. 13, 2007", 6 pgs.

"European Application Serial No. 02766357.4, Communication mailed on Mar. 24, 2009", 2 pgs.

"European Application Serial No. 02766357.4, Communication mailed on Apr. 26, 2005", 2 pgs.

"European Application Serial No. 02766357.4, Communication mailed on May 24, 2006", 4 pgs.

"European Application Serial No. 02766357.4, Response filed Jan. 19, 2007 to Communication mailed on May 24, 2006", 8 pgs.

"European Application Serial No. 02766357.4, Response filed Jun. 23, 2008 to Communication mailed Dec. 13, 2007", 5 pgs.

"European Application Serial No. 02766357.4, Response filed Oct. 5, 2009 to Communication mailed on Mar. 24, 2009", 10 pgs.

"European Application Serial No. 02766357.4, Response filed Nov. 7, 2005 to Communication mailed on Aprl. 26, 2005", 5 pgs.

"European Application Serial No. 04737238.8, Communication mailed Mar. 3, 2006", 4 pgs.

"European Application Serial No. 04737238.8, Communication mailed Mar. 12, 2008", 9 pgs.

"European Application Serial No. 04737238.8, Communication mailed Jul. 25, 2007", 3 pgs.

"European Application Serial No. 04737238.8, Communication mailed Sep. 25, 2006", 4 pgs.

"European Application Serial No. 04737238.8, European Search Report completed May 22, 2007", 4 pgs.

"European Application Serial No. 04737238.8, Response filed Sep. 1, 2006 to Communication mailed Mar. 3, 2006", 7 pgs.

"European Application Serial No. 04737238.8, Response filed Sep. 18, 2008 to Communication mailed Mar. 12, 2008", 7 pgs.

"European Application Serial No. 04737238.8, Response filed Oct. 25, 2006 to Communication mailed Sep. 25. 2006", 2 pgs.

"International Application Serial No. PCT/US02/30414, International Search Report mailed Jan. 8, 2003", 4 pgs.

"International Application Serial No. PCT/US03/22989, International Search Report mailed Dec. 3, 2003", 7 pgs.

"International Application Serial No. PCT/US2004/002332, International Search Report mailed Jan. 28, 2004", 7 pgs.

"International Application Serial No. PCT/US2004/002332, Partial International Search Report mailed Jul. 12, 2004", 4 pgs.

"International Application Serial No. PCT/US2004/002332, Written Opinion mailed Jan. 28, 2004", 7 pgs.

"International Application Serial No. PCT/US99/10142, Internaitonal Search Report mailed Aug. 23, 1999", 6 pgs.

"International Application Serial No. PCT/US2009/002806, International Search Report mailed Dec. 4, 2009", 4 pgs.

"International Application Serial No. PCT/US2009/002806, Written Opinion mailed Dec. 4, 2009", 7 pgs.

"Itamar Medical and Medtronic Announce Further Cooperation to Advance Diagnostic Innovation", *Business Wire*, p. 1254, Full text provided by Dialog, (May 9, 2000), 2 pgs.

"Japanese Application Serial No. 2006-50396, Amendment filed Aug. 17, 2009", (w/ English Translation of Amended Claims), 19 pgs.

"Japanese Application Serial No. 2006-50396, Notification of Reason for Rejection mailed Jan. 25, 2010", (w/ Partial Translation), 3 pgs.

"Japanese Application Serial No. 2006-50396, Notification of Reason for Rejection mailed Feb. 2, 2009", (w/ Partial Translation), 6 pgs.

"Noninvasive MIKRO-TIP Pulse Pressure Transducer Model SPT-301", *Millar Instruments, Inc., Product Information*, (2000), 1 pg.

Auricchio, A, et al., "Can the optimum dosage of resynchronization therapy be derived from the intracardiac electrogram?", *Journal of the American College of Cardiology*, vol. 39, Supplement 1, (Abstract 878-4), (Mar. 6, 2002), p. 124.

Auricchio, A., et al., "The Pacing Therapies for Congestive Heart Failure (PATH-CHF) Study: Rationale, Design, and Endpoints of a Prospective Radomized Multicenter Study", *The American Journal of Cardiology*, 83(5B), (Mar. 11, 1999), 130D-135D.

Auricchio, A., et al., "Cardiac Resynchronization Therapy Restores Optimal Atrioventricular Mechanical Timing in Heart Failure Patients with Ventricular Conduction Delay", *Journal of the American College of Cardiology*, 39(7), (2002), 1163-1169.

Auricchio, A., et al., "Effect of Pacing Chamber and Atrioventricular Delay on Acute Systolic Function of Paced Patients With Congestive Heart Failure", *Circulation*, 99(23), (Jun. 15, 1999), 2993-3001.

Breithardt, O. A., et al., "Acute effects of cardiac resynchronization therapy on left ventricular Doppler indices in patients with congestive heart failure", *American Heart Journal*, vol. 143, No. 1, (Jan. 2002), 34-44.

Breithardt, O. A., et al., "Echocardiographic Quantification of Left Ventricular Asynchrony Predicts an Acute Hemodynamic Benefit of Cardiac Resynchronization Therapy", *Journal of the American College of Cardiology,* vol. 40, No. 3, (2002), 536-545.

Butter, C., et al., "Effect of Resynchronization Therapy Stimulation Site on the Systolic Function of Heart Failure Patients", *Circulation,* 104(25), (Dec. 18, 2001), 3026-3029.

Chen, H. H., et al., "Diastolic Heart Failure in the Community: Clinical Profile, Natural History, Therapy, and Impact of Proposed Diagnostic Criteria", *Journal of Cardiac Failure,* 8(5), (2002), 279-287.

Curtis, J. P., et al., "The Association of Left Ventricular Ejection Fraction, Mortality, and Cause of Death in Stable Outpatients With Heart Failure", *Journal of the American College of Cardiology,* 42(4), (2003), 736-742.

Ding, J., et al., "Cardiac Pacing Using Adjustable Atrio-Ventricular Delays", U.S. Appl. No. 11/049 181, filed Feb. 2, 2005, 35 pgs.

Ding, J., et al., "Method and Apparatus for Setting Pacing Parameters in Cardiac Resynchronization Therapy", U.S. Appl. No. 10/352,780, filed Jan. 28, 2003, 34 pgs.

Kass, D. A., et al., "Improved Left Ventricular Mechanics From Acute VDD Pacing in Patients With Dilated Cardiomyopathy and Ventricular Conduction Delay", *Circulation,* 99(12), (Mar. 30, 1999), 1567-1573.

Kawaguchi, M., et al., "Quantitation of Basal Dyssynchrony and Acute Resynchronization from Left or Biventricular Pacing by Novel Echo-Contrast Variability Imaging", *Journal of the American College of Cardiology,* vol. 39, No. 12, (2002), 2052-2058.

Kerwin, W. F., et al., "Ventricular Contraction Abnormalities in Dilated Cardiomyopathy: Effect of Biventricular Pacing to Correct Interventricular Dyssynchrony", *Journal of the American College of Cardiology,* 35(5), (2000), 1221-1227.

Kim, H., et al., "Integrated MEMS for Pressure Transponder", *1997 International Conference on Solid State Sensors and Actuators. Transducers '97,* vol. 2., (Chicago, IL), (1997), 1011-1014.

Kramer, A. P., et al., "Method and Apparatus for Adjustment of Sequential Biventricular Pacing", U.S. Appl. No. 10/742,630, filed Dec. 19, 2003, 41 pgs.

Kramer, A. P, et al., "Automatic Selection From Multiple Cardiac Optimization Protocols", U.S. Appl. No. 10/624,458, filed Jul. 21, 2003, 49 pgs.

Le Rest, C., et al., "Use of left ventricular pacing in heart failure: Evaluation by gated blood pool imaging", *Journal of Nuclear Cardiology,* vol. 6, No. 6, (Nov./Dec. 1999), 651-656.

Little, W. C., et al., "Clinical Evaluation of Left Ventricular Diastolic Performance", *Progress in Cardiovascular Disease,* 32(4), (1990), 273-290.

Min, M., et al., "Electrical Impedance and Cardiac Monitoring—Technology, Potential and Applications", *International Journal of Bioelectromagnetism,* 5(1), (2003), 53-56.

Nelson, G. S., et al., "Left ventricular or biventricular pacing improves cardiac function at diminished energy cost in patients with dilated cardiomyopathy and left bundle-branch block", *Circulation,* 102(25), (Dec. 19, 2000), 3053-3059.

Nelson, G. S., et al., "Predictors of Systolic Augmentation From Left Ventricular Preexcitation in Patients with Dilated Cardiomyopathy and Intraventricular Conduction Delay", *Circulation,* 101, (Jun. 13, 2000), 2703-2709.

Prinzen, F. W., et al., "Mapping of regional myocardial strain and work during ventricular pacing: experimental study using magnetic resonance imaging tagging", *Journal of the American College of Cardiology,* 33(6), (May 1999), 1735-1742.

Redfield, M. M., et al., "Burden of Systolic and Diastolic Ventricular Dysfunction in the Community", *JAMA,* 289(2), (2003), 194-202.

Ritter, P., et al., "A Built-In System Based on the Peak Endocardial Acceleration (PEA) for AV-Delay Optimization in DDDR Pacing", *PACE,* 20(5) (Part II), (Abstract of Paper presented at EUROPACE '97), (May 1997), 1567.

Sheiban, I., et al., "Time course and determinants of left ventricular function recovery after primary angioplasty in patients with acute myocardial infarction", *J Am Coll Cardiol.,* 38(2), (Aug. 2001), 464-471.

Søgaard, P., et al., "Impact of Acute Biventricular Pacing on Left Ventricular Performance and Volumes in Patients with Severe Heart Failure: a tissue Doppler and three-dimensional echocardiographic study", *Cardiology,* 95, (2001), 173-182.

Stellbrink, C., et al., "Impact of Cardiac Resynchronization Therapy Using Hemodynamically Optimized Pacing on Left Ventricular Remodeling in Patients With Congestive Heart Failure and Ventricular Conduction Disturbances", *Journal of the American College of Cardiology,* vol. 38, No. 7, (Dec. 2001), 1957-1965.

Watanabe, M., et al., "Developmental Remodeling and Shortening of Cardiac Outflow Tract Involves Myocyte Programmed Cell Death", *Development,* 125(19), (1998), 3809-3820.

Xiao, H. B, et al., "Differing effects of right ventricular pacing and left bundle branch on left ventricular function", *British Heart Journal,* vol. 69, No. 2, (Feb. 1993), 166-173.

Yu, C.-M., et al., "High Prevalence of Left Ventricular Systolic and Diastolic Asynchrony in Patients With Congestive Heart Failure and Normal QRS Duration", *Heart,* vol. 89, (2003), 54-60.

Yu, C.-M., et al., "Tissue Doppler Echocardiographic Evidence of Reverse Remodeling and Improved Synchronicity by Simultaneously Delaying Regional Contraction After Biventricular Pacing Therapy in Heart Failure", *Circulation,* 105 (2002), 438-445.

Zile, M. R., et al., "Diastolic Heart Failure: Diagnosis and Treatment", *Clinical Cornerstone,* 3(2), [online]. [retrieved Jul. 16, 2007]. Retrieved from the Internet: <URL: http://cardiology.medscape.com/ExcerptaMed/ClinCornerstne/200.../pnt- clc0302.03.zile.htm, (2001), 14 pgs.

"U.S. Appl. No. 11/049,181, Notice of Allowance mailed Apr. 22, 2010", 4 pgs.

"U.S. Appl. No. 11/049,181, Notice of Allowance mailed Aug. 11, 2010", 6 pgs.

"U.S. Appl. No. 11/049,181, Response filed Apr. 5, 2010 to Final Office Action mailed Feb. 4, 2010", 6 pgs.

"U.S. Appl. No. 11/567,933, Non Final Office Action mailed Nov. 17, 2010", 6 pgs.

"U.S. Appl. No. 11/567,933, Notice of Allowance", 7 pgs.

"U.S. Appl. No. 11/567,933, Response filed Feb. 17, 2011 to Non Final Office Action mailed Nov. 17, 2010", 6 pgs.

"U.S. Appl. No. 11/567,933, Restriction Requirement mailed Sep. 16, 2010", 7 pgs.

"U.S. Appl. No. 12/424,136, Final Office Action mailed Mar. 18, 2011", 6 pgs.

"U.S. Appl. No. 12/424,136, Non Final Office Action mailed Nov. 19, 2010", 7 pgs.

"U.S. Appl. No. 12/424,136, Notice of Allowance mailed Jun. 2, 2011", 5 pgs.

"U.S. Appl. No. 12/424,136, Response filed May 18, 2011 to Final Office Action mailed Mar. 18, 2011", 7 pgs.

"U.S. Appl. No. 12/955,218 , Response filed Aug. 15, 2011 to Non Final Office Action mailed May 13, 2011", 9 pgs.

"U.S. Appl. No. 12/955,218, Non Final Office Action mailed May 13, 2011", 8 pgs.

"Japanese Application Serial No. 2006-503096, Notice of Allowance mailed Jan. 25, 2011", 3 pgs.

"Japanese Application Serial No. 2006-503096, Office Action Mailed Jul. 29, 2010", 1 pg.

"Japanese Application Serial No. 2006-503096, Response filed Dec. 22, 2010 to Non Final Office Action mailed Jul. 29, 2010", 19.

"U.S. Appl. No. 12/955,218, Notice of Allowance mailed Sep. 22, 2011", 8 pgs.

"Japanese Application Serial No. 2011-508500, Office Action mailed Aug. 9, 2012", With English Translation, 4 pgs.

"Japanese Application Serial No. 2011-508500, Office Action mailed Feb. 12, 2013", With English Translation, 11 pgs.

"Japanese Application Serial No. 2011-508500, Response filed Nov. 7, 2012 to Office Action mailed Aug. 9, 2012", With English Claims, 7 pg.

\* cited by examiner

| | | 1402 | 1404 SMARTDELAY-IPT INPUTS | 1406 |
|---|---|---|---|---|
| 1440 | | 1) INTERVENTRICULAR DELAY | 2) LV LEAD LOCATION | 3) INTRINSIC AV INTERVALS |
| 1442 AUTOMATIC MODE | OPERATION MODE DETERMINED BY LV SENSING | | | |
| | LV SENSING = DEDICATED BIPOLAR (TIP >> RING) | DEVICE DETERMINES RVS TO LVS | DEVICE DETERMINES LV LEAD LOCATION | USER INPUT OF TEMPORARY PACED LRL DEVICE DETERMINES: AS TO RVS, AS TO LVS AP TO RVS, AP TO LVS |
| 1444 MANUAL MODE | LV SENSING = EXTENDED BIPOLAR (TIP >> COIL) | USER INPUT OF INTRINSIC QRS WIDTH | DEVICE DETERMINES LV LEAD LOCATION | USER INPUT OF TEMPORARY PACED LRL DEVICE DETERMINES: AS TO RVS, AS TO LVS AP TO RVS, AP TO LVS |

☐ = USER INPUT REQUIRED

*Fig. 4*

SMARTDELAY-IPT AVD:
SMALL STRESS: SHORT AVD (LOOSE ATRIAL KICK)
    = 10 - 20% OF AV INTERVAL
MEDIUM STRESS: LONG AVD (DYSSYNCHRONOUS CONTRACTION, MR)
    = 80 - 95% OF AV INTERVAL
LARGE STRESS: SHORT/LONG AVD WITH VV DELAY
    = AVD WITH RV PRE-EXCITATION FOR LBB (OR LV PRE-EXCITATION FOR RBB)

SMART DELAY FOR INTERMITTENT STRESS THERAPY

CROSS REFERENCE TO RELATED APPLICATIONS

This application claims the benefit of U.S. Provisional Application No. 61/051,529, filed on May 8, 2008, under 35 U.S.C. §119(e), which is hereby incorporated by reference.

This application is related to commonly assigned U.S. Pat. No. 7,110,817, entitled "Method and Apparatus for Optimizing Stroke Volume During DDD Resynchronization Therapy Using Adjustable Atrio-Ventricular Delays," issued on Sep. 19, 2006, which is incorporated herein by reference.

TECHNICAL FIELD

This application relates generally to medical devices and, more particularly, to systems, devices and methods for implementing intermittent stress therapy.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. These pumping functions are resulted from contractions of the myocardium. In a normal heart, the sinoatrial node, the heart's natural pacemaker, generates electrical impulses that propagate through an electrical conduction system to various regions of the heart to excite the myocardial tissues of these regions. Coordinated delays in the propagations of the electrical impulses in a normal electrical conduction system cause the various portions of the heart to contract in synchrony to result in efficient pumping functions. A blocked or otherwise abnormal electrical conduction and/or deteriorated myocardial tissue cause dysynchronous contraction of the heart, resulting in poor hemodynamic performance, including a diminished blood supply to the heart and the rest of the body. The condition where the heart fails to pump enough blood to meet the body's metabolic needs is known as heart failure.

Myocardial infarction (MI) is the necrosis of portions of the myocardial tissue resulted from cardiac ischemia, a condition in which the myocardium is deprived of adequate oxygen and metabolite removal due to an interruption in blood supply caused by an occlusion of a blood vessel such as a coronary artery. The necrotic tissue, known as infarcted tissue, loses the contractile properties of the normal, healthy myocardial tissue. Consequently, the overall contractility of the myocardium is weakened, resulting in an impaired hemodynamic performance. Following an MI, cardiac remodeling starts with expansion of the region of infarcted tissue and progresses to a chronic, global expansion in the size and change in the shape of the entire left ventricle. The consequences include a further impaired hemodynamic performance and a significantly increased risk of developing heart failure, as well as a risk of suffering recurrent MI.

Heart disease such as MI and/or heart failure can cause adverse ventricular remodeling and an imbalance in autonomic tone favoring sympathetic activity over parasympathetic tone. During heart disease, the compromised ventricles may be less than capable of maintaining normal cardiac output. As a result, the body compensates for the reduced cardiac output by increasing sympathetic tone and suppressing parasympathetic activity, resulting in increased heart rate, myocardial contractility and blood volume. This mechanism is acutely beneficial, but has a long-term deleterious effect.

It has been shown experimentally that intermittent stress such as exercise, dobutamine infusion, myocardial pacing, or external counterpulsation provides beneficial conditioning effects for the heart and body. Intermittent stress (e.g. exercise) improved the imbalance in the autonomic tone, as the autonomic tone trended from a predominantly sympathetic tendency toward a desired autonomic balance between the sympathetic and parasympathetic systems. For example, intensive exercise training in patients with reduced ventricular function has been shown to result in a significant improvement in exercise capacity (increased $O_2$ uptake, maximum minute ventilation, $CO_2$ production, exercise time and watts), with no deleterious effects on left ventricular volume, function or wall thickness. A potential mechanism for the benefit may be that these short intervals of stress increase sympathetic tone and cause a reflexive increase in parasympathetic tone after the stress is discontinued. Many HF and post-MI patients, however, are either debilitated and cannot exercise or do not tolerate exercise well enough to exercise effectively.

Intermittent sympathomimetic stimulation in animals with dobutamine produces benefits analogous to those of physical conditioning. In a pilot clinical study, patients with stable moderate severe HF (EF=23%) who received dobutamine therapy (30 min/day, 4 days/week, 3 weeks) experienced the following benefits: increased exercise tolerance; improved heart rate variability; lowered peripheral vascular resistance; and reduced plasma noradrenaline.

It has been proposed to deliver intermittent stress in the form of artificial cardiac pacing as a potential therapy for cardiac disease. A patient may not experience the desired benefit if the pacing delivers too little stress, or may be harmed (similar to over-exercising) if the pacing delivers too much stress.

SUMMARY

A pacing system delivers cardiac protection pacing to protect the heart from injuries. The pacing system receives a set of inputs and calculates parameters for delivering optimized cardiac protection pacing tailored for different stress levels and QRS intervals. The system automatically adjusts heart rate to optimize cardiac protection pacing in a closed-loop system.

In one embodiment, a method for delivering pacing pulses for cardiac protection is provided. Intrinsic atrioventricular (AV) intervals are sensed. The intrinsic AV interval and a predetermined equation relating the AV interval to an optimal AV delay are used to provide a maximum positive rate of left ventricular pressure change during systole. An AV delay is calculated using a predetermined percentage of the optimal AV delay to deliver ventricular pacing pulses to provide a desired level of stress for cardiac protective pacing therapy (CPPT) to provide a cardiac conditioning therapy to improve autonomic balance. According to various embodiments, one or more of LV electrode location, intrinsic interventricular (VV) interval, and QRS width are sensed or received, and the AV delay is calculated based on the sensed or received parameters.

In one embodiment, a method for operating a cardiac pacing device is provided. Cardiac protective pacing therapy (CPPT) is delivered to provide a cardiac conditioning therapy to improve autonomic balance to one or more ventricular sites in an atrial tracking pacing mode with an atrioventricular (AV) delay. One or more of intrinsic interventricular (VV) timing, QRS width, left ventricular (LV) electrode location, and intrinsic AV intervals are sensed or received. AV delay is modulated based on the sensed or received parameters, including calculating AV delay using the sensed or received parameters and a predetermined equation relating the parameters to an optimal AV delay, and using a predetermined percentage of the optimal AV delay to deliver ventricular pacing pulses to provide a desired level of stress for the CPPT. Heart rate (HR) is sensed in response to the pacing pulses. Parameters of the AV delay are dynamically adjusted for the cardioprotective pacing pulse based on the sensed HR in a closed loop system.

In one embodiment, a system for calculating atrioventricular (AV) delay is provided. The system includes a signal input to receive at least one cardiac signal indicative of cardiac events including at least one atrial event and one ventricular event and an event detector, coupled to the signal input, to detect the at least one atrial event and one ventricular event. The system also includes a measurement module, coupled to the event detector, to measure an AV time interval between an atrial event and a ventricular event of the at least one atrial event and one ventricular event. The system further includes an AV delay calculator coupled to the measurement module, the AV delay calculator adapted to calculate an AV delay using the AV interval and a predetermined equation relating the AV interval to an optimal AV delay to provide a maximum positive rate of left ventricular pressure change during systole, and further adapted to calculate a percentage of the optimal AV delay to deliver ventricular pacing pulses to provide a desired level of stress for cardiac protective pacing therapy (CPPT) to provide a cardiac conditioning therapy to improve autonomic balance.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

FIG. 4 illustrates a method for calculating parameters for CPPT, according to various embodiments of the present subject matter.

DETAILED DESCRIPTION

Figure 1A:
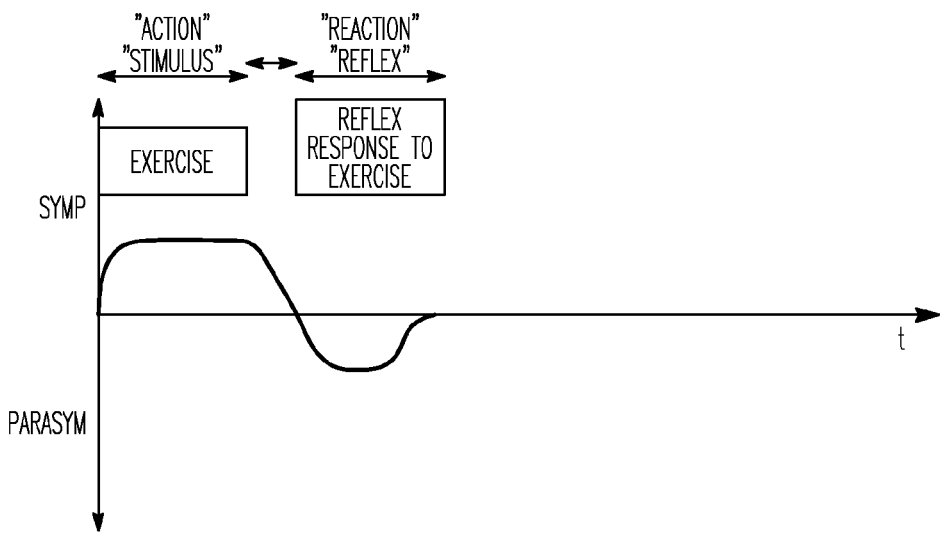
FIG. 1A illustrates the autonomic response to a period of exercise.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter delivers cardiac protective pacing therapy (CPPT) to protect the heart from injuries. CPPT is intermittently delivered to intermittently provide a desired stress to the heart, as evidenced by an increase in sympathetic tone during the pacing. CPPT may also be referred to as an intermittent pacing therapy (IPT) to condition the heart. The pacing system, utilizing a method sometimes referred to as SmartDelay-IPT, receives a set of inputs and calculates parameters for delivering optimized cardiac protection pacing tailored for different stress levels and QRS intervals. The system automatically adjusts heart rate to optimize cardiac protection pacing in a closed-loop system. According to various embodiments, CPPT is triggered by a programmed or predetermined schedule (e.g. only at night). The present subject matter delivers CPPT to post-MI and heart failure patients to control expansion of the infarct region and for remodeling, and can be delivered alone or in combination with other therapies such as cardiac resynchronization therapy (CRT).

In one embodiment, a method for delivering pacing pulses for cardiac protection is provided. Intrinsic atrioventricular (AV) intervals are sensed. Intrinsic AV intervals include atrial sensed or atrial paced to ventricular sensed intervals. The intrinsic AV interval and a predetermined equation relating the AV to an optimal AV delay are used to provide a maximum positive rate of left ventricular pressure change during systole. An AV delay (also referred to as AVD) is calculated using a predetermined percentage of the optimal AVD to deliver ventricular pacing pulses to provide a desired level of stress for cardiac protective pacing therapy (CPPT) to provide a cardiac conditioning therapy to improve autonomic balance. According to various embodiments, one or more of LV electrode location, intrinsic interventricular (VV) interval, and QRS width are sensed or received, and the AVD is calculated based on the sensed or received parameters. Sensing intrinsic VV interval includes an RV sense event to an LV sense event in an embodiment. In other embodiments, intrinsic VV interval includes one ventricular paced event to a sensed event in the other ventricle. Thus, the intrinsic VV interval includes one ventricular sensed or paced event to another ventricular sensed event.

Sensed AV offset is to offset the sensing delay (or time interval between the actual cardiac depolarization and its detection), and is a function of sensing circuit delays in various embodiments. For example, a more aggressive therapy (increase stress) may be delivered by shortening the AV delay, pacing at a faster rate, providing longer periods of pacing, or providing longer VV delays (e.g. a longer time between a right ventricular pace and a left ventricular pace as there is normally very little time delay between the two). A more conservative therapy (decrease stress) may be delivered by lengthening the AV delay, pacing at a slower rate, providing shorter periods of pacing, or providing shorter VV delays.

According to an embodiment, a single ventricular pacing site is used to deliver CPPT. Multiple ventricular pacing sites are used in other embodiments. The multiple pacing cites are stimulated using one or more multi-polar ventricular leads providing options to change or introduce multiple VV delays to create stress for CPPT pacing, in various embodiments.

Autonomic tone may be modulated by stimulating or inhibiting an autonomic neural target. Embodiments of the present subject mater modulate autonomic tone using CPPT. Physiology associated with CPPT is discussed below.

The sinoatrial (SA) node generates electrical impulses that propagate through an electrical conduction system to various regions of the heart to excite the myocardial tissues of these regions. An intrinsic heart rhythm may be a normal rhythm or an abnormal rhythm. Coordinated delays in the propagations of the electrical impulses in a normal electrical conduction system cause the various portions of the heart to contract in synchrony. Synchrony, as used herein, indicates a coordinated contraction of the various portions of the heart to result in efficient pumping functions. Synchrony does not indicate that all of the portions of the heart contract at the same time.

Abnormal electrical conduction and/or deteriorated myocardial tissue cause asynchrony (no coordinated timing) between the various portions of the heart, which result in inefficient pumping functions. The present subject matter uses cardiac protective pacing therapy (CPPT) to provide a cardiac conditioning therapy to improve autonomic balance, and thus improve the health of the heart. CPPT is an intermittent pacing therapy that paces the heart in such a manner as to intentionally stress the heart during intermittent periods. When the heart is stressed with CPPT, the heart is paced, forcing the heart to work harder in comparison to a time when CPPT is not applied to the heart. The paced heart works harder in local regions of the heart away from a site where the stress-inducing pacing pulses are delivered. For example, a stressed heart may be paced to beat faster and/or more asynchronous (less coordinated). By way of example and not limitation, various CPPT embodiments increase the pacing rate for the right atrium, increase the pacing rate for the right ventricle, shorten an AV delay, and/or lengthen the VV delay. Increasing the intensity of the CPPT may involve further increasing the pacing rate of the right atrium or right ventricle, further shortening the AV delay to be more different from the intrinsic rate without CPPT, altering the pacing site, and/or further lengthening of the VV delay to be more different from the intrinsic rate without CPPT. In patients who have dysynchrony and receive biventricular pacing for the dysynchrony, cardiac stress can be increased by discontinuing the biventricular pacing during the sequence of stress inducing pacing pulses. Decreasing the intensity of the CPPT may involve altering the pacing site, may involve reducing the pacing rate of the right atrium or right ventricle closer to the intrinsic rate, may involve increasing the AV delay closer to the intrinsic AV delay, and/or may involve shortening the VV delay closer to the intrinsic VV delay (whether or not the intrinsic rhythm is normal or abnormal). Delivering CPPT with higher intensity (not stress) corresponds to increasing the sympathetic response during the CPPT.

Diseases

The present subject matter can be used to prophylactically or therapeutically treat various diseases by modulating autonomic tone. Examples of such diseases or conditions include hypertension, cardiac remodeling, and heart failure.

Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

Following myocardial infarction (MI) or other cause of decreased cardiac output, a complex remodeling process of the ventricles occurs that involves structural, biochemical, neurohormonal, and electrophysiologic factors. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilation. As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction (decompensation). It has been shown that the extent of ventricular remodeling is positively correlated with increased mortality in post-MI and heart failure patients.

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease. Heart failure patients have reduced autonomic balance, which is associated with LV dysfunction and increased mortality. Modulation of the sympathetic and parasympathetic nervous systems has potential clinical benefit in preventing remodeling and death in heart failure and post-MI patients. Direct electrical stimulation can activate the baroreflex, inducing a reduction of sympathetic nerve activity and reducing blood pressure by decreasing vascular resistance. Sympathetic inhibition and parasympathetic activation have been associated with reduced arrhythmia vulnerability following a myocardial infarction, presumably by increasing collateral perfusion of the acutely ischemic myocardium and decreasing myocardial damage.

Therapy Protocols

The present subject matter modulates autonomic tone using CPPT. Preconditioning of the myocardium occurs as a prophylactic therapy in preparation for an anticipated event. For example, the myocardium can be preconditioned in anticipation for surgery, or can be preconditioned based on observed or detected events that indicate an increased probability of an upcoming ischemic event. Examples of such events include a previous myocardial infarction and angina. Prophylactic conditioning can be used to modulate autonomic tone from higher sympathetic tendencies toward an autonomic balance to improve the health of a patient prone to heart failure, hypertension and remodeling. Postconditioning of the myocardium occurs as a therapeutic treatment to a disease. For example, postconditioning of the myocardium can reduce the size of any infarct area caused by the ischemic event. For example, the postconditioning therapy can be triggered based on commands received from a patient or physician after observing a myocardial infarction, or a physician can deliver postconditioning therapy after a surgical procedure for which the heart was stopped. In an embodiment, the device detects an ischemic event or other event indicated for postconditioning therapy, and automatically delivers the postconditioning therapy. The postconditioning therapy can occur during the time of reperfusion, for a time after reperfusion, or during and for a time after reperfusion.

A cardiac conditioning therapy may also be referred to as a cardiac protective therapy, as it is protects against the deleterious effects of an autonomic tone with an undesirably high sympathetic tendency. The cardiac conditioning therapy may mimic the effects of exercise.

FIG. 1A illustrates the autonomic response to a period of exercise. Exercise is a stimulus that increases the sympathetic response. After the period of exercise ends, a reflex response to the exercise increases the parasympathetic tone. The parasympathetic response appears to be a reaction to the sympathetic action of exercise. Those of ordinary skill in the art will understand that the illustrated graph is a simple illustration. The horizontal axis represents time, and the vertical axis represents the autonomic tone. For simplicity, the value of the vertical axis corresponding to the horizontal axis represents the autonomic balance (the balance between the sympathetic and parasympathetic neural activity). Those of ordinary skill in the art will know that, over time, as the health of the heart improves and the autonomic balance improves by having a more parasympathetic tone, the horizontal axis (representing the autonomic balance) will trend more toward the parasympathetic tone. By way of an everyday example of exercise, it is noted that a runner's resting heart rate tends to lower as the runner's conditioning improves. This example indicates that running, which temporarily increases sympathetic tone as evidenced by an increased heart rate, will trend the autonomic balance of the runner toward a more parasympathetic tone.

Figure 1B:
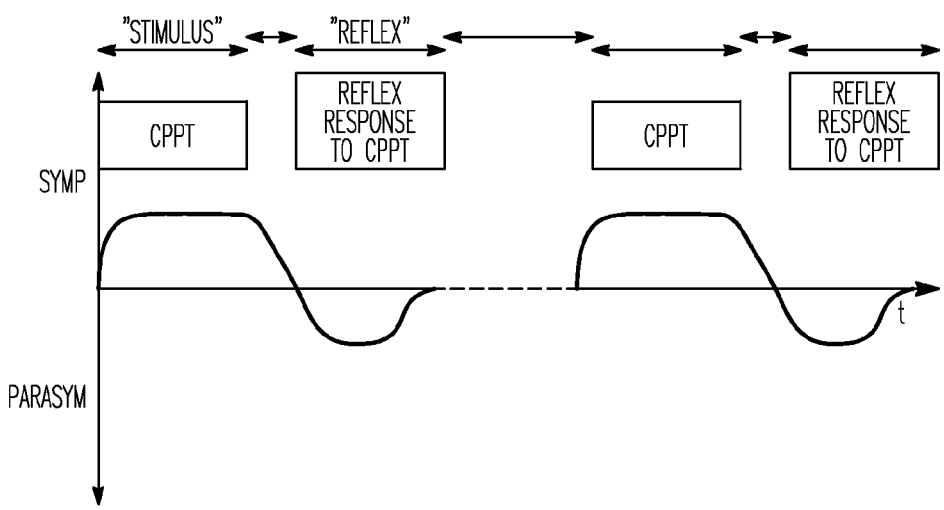
FIG. 1B illustrates the autonomic response to a period of cardiac protective pacing therapy (CPPT).

FIG. 1B illustrates the autonomic response to a period of CPPT. Similar to the period of exercise, CPPT is a stimulus that increases the sympathetic response during the period of pacing, and results in a reflex response that increases parasympathetic tone after the pacing ends. As illustrated, the CPPT functions as a stimulus that provides a sympathetic component (action) that generates a desired parasympathetic reflex (reaction to the action). A cardiac conditioning therapy may correspond to recommended exercises periods (e.g. 30 to 60 minutes, two times per day). Various therapy durations and frequencies can be used. Various cardiac conditioning therapies are programmed according to a schedule. Various cardiac conditioning therapies are programmed to occur after a detected event such as a period of exercise by the patient.

Figure 2:
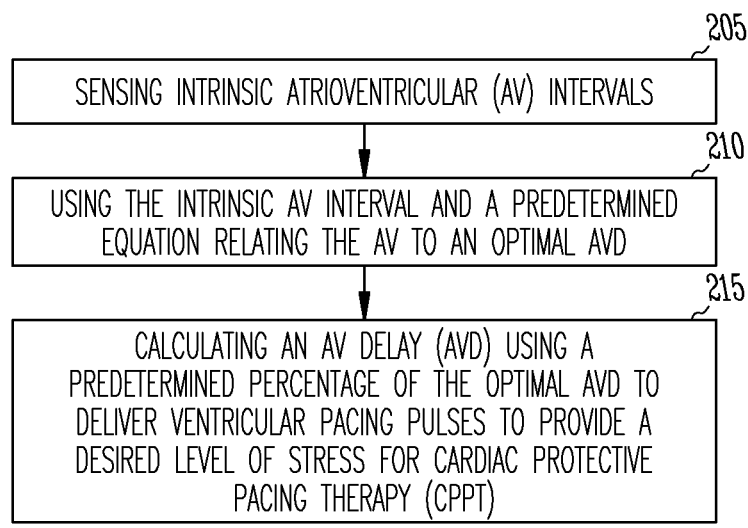
FIG. 2 is a flow chart illustrating an embodiment of a method for delivering pacing pulses for cardiac protection.

FIG. 2 is a flow chart illustrating an embodiment of a method for delivering pacing pulses for cardiac protection. Intrinsic atrioventricular (AV) intervals are sensed, at 205. At 210, the intrinsic AV interval and a predetermined equation relating the AV interval to an optimal AV delay are used to provide a maximum positive rate of left ventricular pressure change during systole, LV+dp/dt. An AV delay (AVD) is calculated at 215, using a predetermined percentage of the optimal AVD to deliver ventricular pacing pulses to provide a desired level of stress for cardiac protective pacing therapy (CPPT) to provide a cardiac conditioning therapy to improve autonomic balance. According to various embodiments, one or more of LV electrode location, intrinsic interventricular (VV) interval, and QRS width are sensed or received, and the AVD is calculated based on the sensed or received parameters.

The SmartDelay-IPT method is also a function of QRS width. QRS width is equivalent to the RV-LV interval (VV interval). Generally, QRS width is sensed from a surface ECG, and VV interval is sensed from an intracardiac electrogram. The method further includes, in various embodiments, measuring QRS width and modulating the variably shortened AV delay based on the sensed QRS width. Modulating the AV delay includes calculating a first AVD for a wide QRS width and a second AVD for a narrow QRS width, according to various embodiments. AV delay and VV delay are also functions of QRS width, according to various embodiments. In one embodiment, a wide QRS width includes QRS width greater than approximately 150 msec. A narrow QRS width includes QRS width greater than approximately 120 msec and less then approximately 150 msec, in an embodiment. Various method embodiments also include sensing heart rate (HR) in response to the pacing sequences and dynamically adjusting parameters of the AV delay for the CPPT based on the sensed HR.

Figure 3:
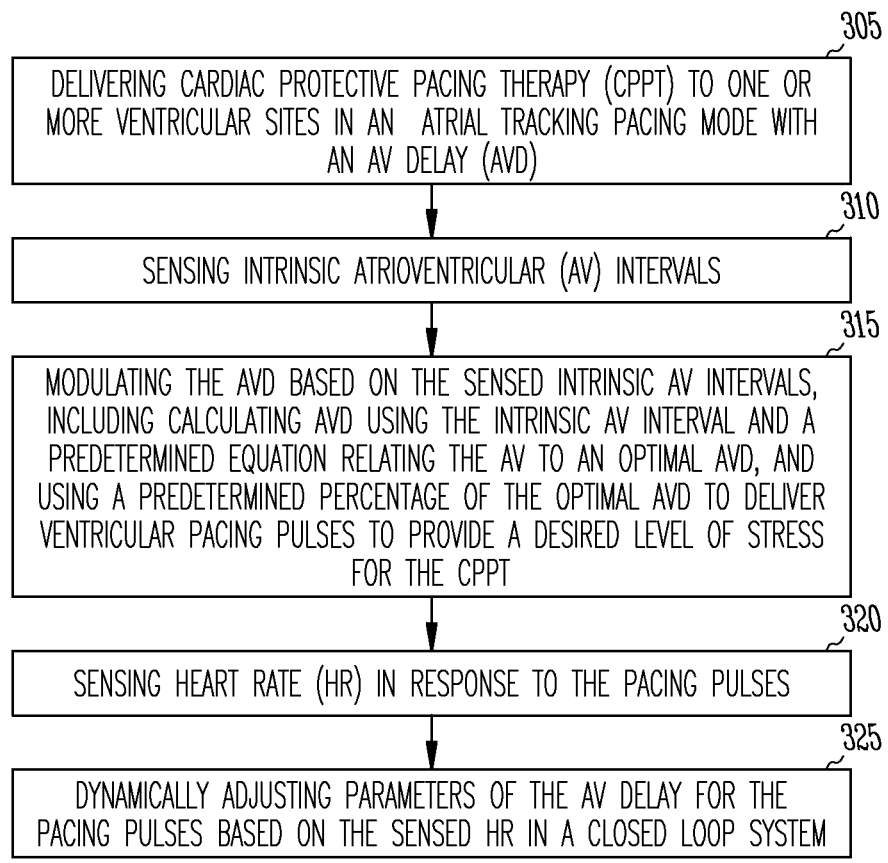
FIG. 3 is a flow chart illustrating an embodiment of method for operating a cardiac pacing device.

FIG. 3 is a flow chart illustrating an embodiment of method for operating a cardiac pacing device. At 305, cardiac protective pacing therapy (CPPT) is delivered to provide a cardiac conditioning therapy to improve autonomic balance to one or more ventricular sites in an atrial tracking pacing mode with an AV delay (AVD). At 310, intrinsic AV intervals are sensed. AVD is modulated based on the sensed or received parameters at 315, including calculating AVD using the sensed or received parameters and a predetermined equation relating the parameters to an optimal AVD, and using a predetermined percentage of the optimal AVD to deliver ventricular pacing pulses to provide a desired level of stress for the CPPT. Heart rate (HR) is sensed in response to the pacing pulses, at 320. At 325, parameters of the AV delay are dynamically adjusted for the cardioprotective pacing pulse based on the sensed HR in a closed loop system.

According to one embodiment, LV electrode location is received, and the AVD is modulated or adjusted using the LV electrode location. LV electrode (or LV lead) location can be sensed by the device or entered by the programmer, in various embodiments. Intrinsic interventricular (VV) interval is sensed and the AVD modulated using the sensed intrinsic VV interval, in an embodiment. In various embodiments, QRS width is sensed and the AVD is modulated using the sensed QRS width. Modulating AVD for the cardio protective pacing pulses includes determining the delay as a percentage of an intrinsic AV interval, in an embodiment. Modulating AVD includes using a short AVD to provide a small amount of stress during cardioprotective pacing, such as using an AVD that is 10 to 20 percent of the intrinsic AV interval in an embodiment. Modulating AVD includes using a long AVD to provide a medium amount of stress during cardioprotective pacing, such as using an AVD that is 80 to 95 percent of the intrinsic AV interval in an embodiment. In one embodiment, modulating AVD includes using an AVD and a VV delay to provide a large amount of stress during cardioprotective pacing.

FIG. 4 illustrates a method for calculating parameters for CPPT, according to various embodiments of the present subject matter. According to various embodiments, methods for calculating parameters for CPPT or IPT are referred to as SmartDelay-IPT methods, as the methods are used optimize AV and/or VV delay parameters for the delivery of CPPT. The illustrated method has an automatic mode 1442 and a manual mode 1444, where the operation mode is determined by LV sensing 1440. According to various embodiments, interventricular delay input 1402 is sensed in automatic mode or provided via user input in manual mode. LV lead location input 1404 is recorded in the device by a user during programming, in an embodiment. LV lead location input 1404 is sensed by the implanted device, in various embodiments. Intrinsic AV interval input 1406 includes both sensed and user input components in both automatic and manual mode, in various embodiments.

Figure 5:
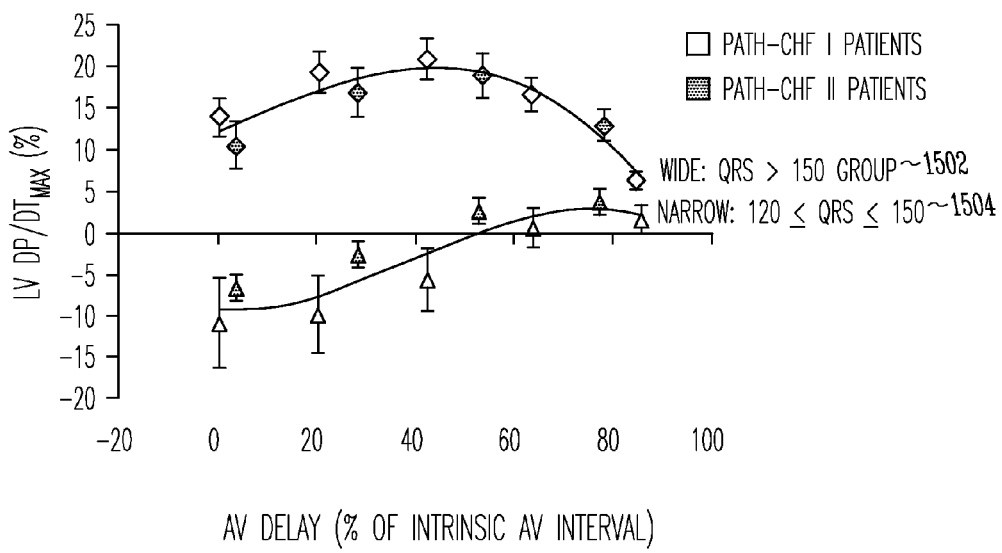
FIGS. 5-9 are graphical displays illustrating calculated parameters for CPPT, according to various embodiments.

FIGS. 5-9 are graphical displays illustrating calculated parameters for CPPT, according to various embodiments. FIG. 5 illustrates an embodiment where CPPT is delivered using a modulated AV delay, and the AV delay limits are recommended by the SmartDelay-IPT method. In the depicted embodiment, the SmartDelay-IPT method recommends different AV delay limits based on the QRS width of the patient receiving the therapy. According to various embodiments, a wide QRS width 1502 includes QRS width greater than 150 msec and a narrow QRS width 1504 includes QRS width greater than about 120 msec and less then about 150 msec.

Figure 6:
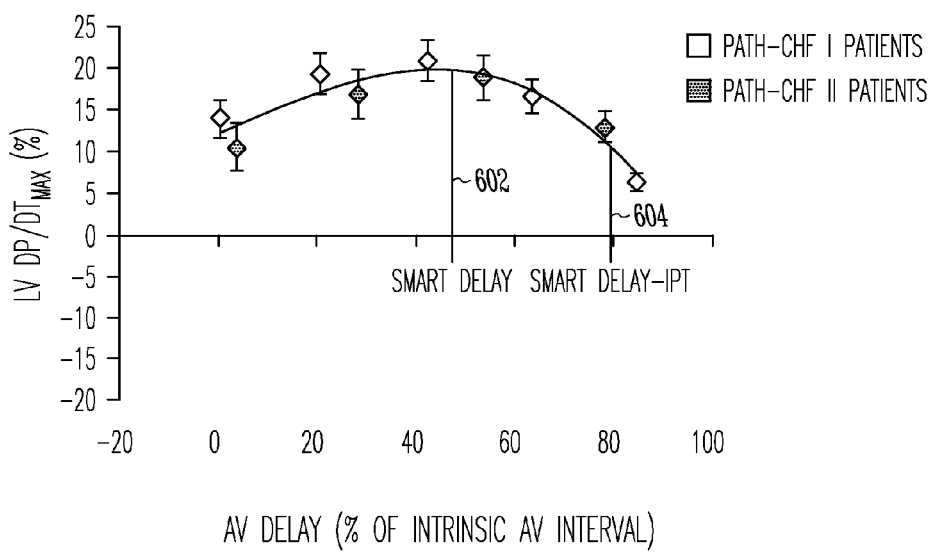

FIG. 6 illustrates an embodiment where an AV delay is recommended for CPPT for a given patient having a relatively wide QRS. In the depicted embodiment, the SmartDelay method calculates an AV delay 602 for optimal output. Smart-Delay refers to a parameter optimization method for CRT, and SmartDelay-IPT refers to a parameter optimization method for IPT/CPPT. A percentage of the calculated AV delay is selected using the SmartDelay-IPT method to provide a limit for CPPT. In an embodiment, a long AV delay 604 is selected, that is 80-95% of the AV interval. This AV delay is the limit at which pacing is turned off. This method assumes that the intrinsic conduction is dysynchronous, and allows more intrinsic dominant activation, in various embodiments.

Figure 7:
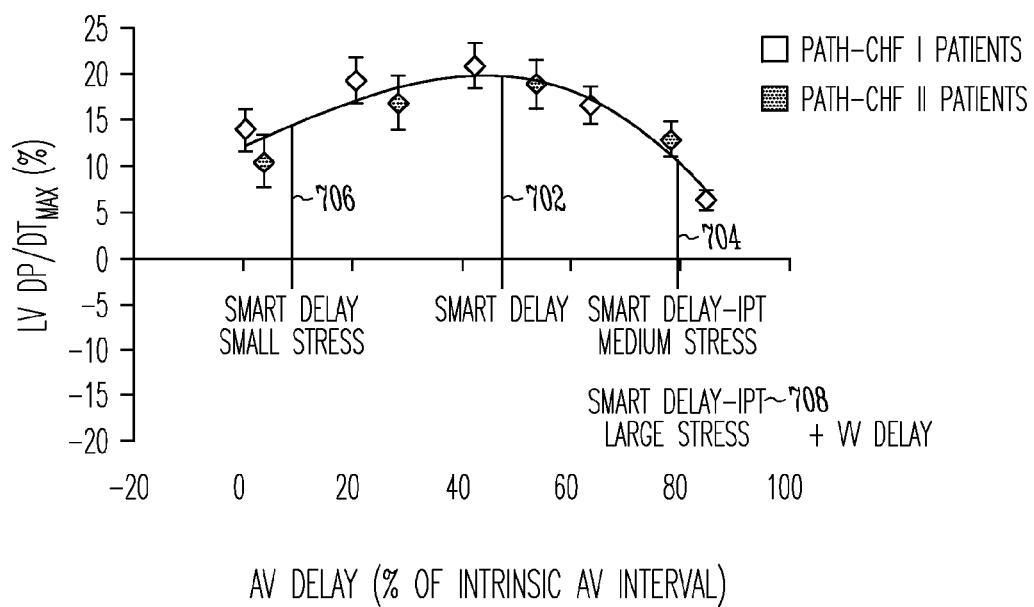

FIG. 7 illustrates an embodiment where various AV delays are recommended for CPPT for a given patient having a relatively wide QRS, based on the amount of stress desired in the delivered CPPT. In one embodiment, a user (physician or other qualified medical personnel) selects the AV delay based on various factors (patient's condition, lifestyle, etc.). In the depicted embodiment, the SmartDelay method calculates an AV delay 702 for optimal output. A percentage of the calculated optimal AV delay is selected using the SmartDelay-IPT method to provide a limit for CPPT. In an embodiment, a relatively small amount of stress (as delivered by the CPPT) is desired, and a short AV delay 706 is selected, that is 10-20% of the AV interval. In one embodiment, a relatively medium amount of stress is desired, and a long AV delay 704 is selected, that is 80-95% of the AV interval. A relatively large amount of stress is desired in an embodiment 708, and a short or long AV delay with an additional VV delay is selected. According to various embodiments, a particular stress level is selected for each duration of CPPT delivered, and can be re-selected via the device controller or via user input (medical professional) for further therapy. In addition, the parameters can be adjusted using a closed loop system based on sensed heart-related parameters, such as heart rate (HR) in an embodiment.

Figure 8:
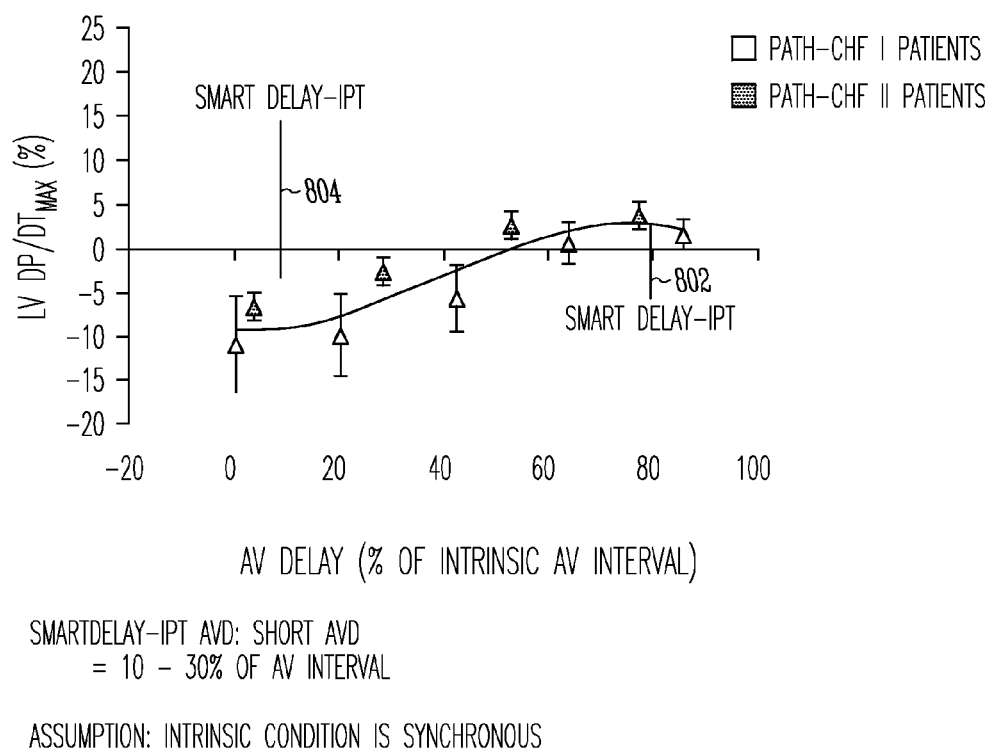

FIG. 8 illustrates an embodiment where an AV delay is recommended for CPPT for a given patient having a relatively narrow QRS. In the depicted embodiment, the SmartDelay method calculates an AV delay 802 for optimal output. A percentage of the calculated AV delay is selected using the SmartDelay-IPT method to provide a limit for CPPT. In an embodiment, a short AV delay 804 is selected, that is 10-30% of the AV interval. This AV delay is the limit at which pacing is turned off. This method assumes that the intrinsic conduction is synchronous, in various embodiments.

Figure 9:
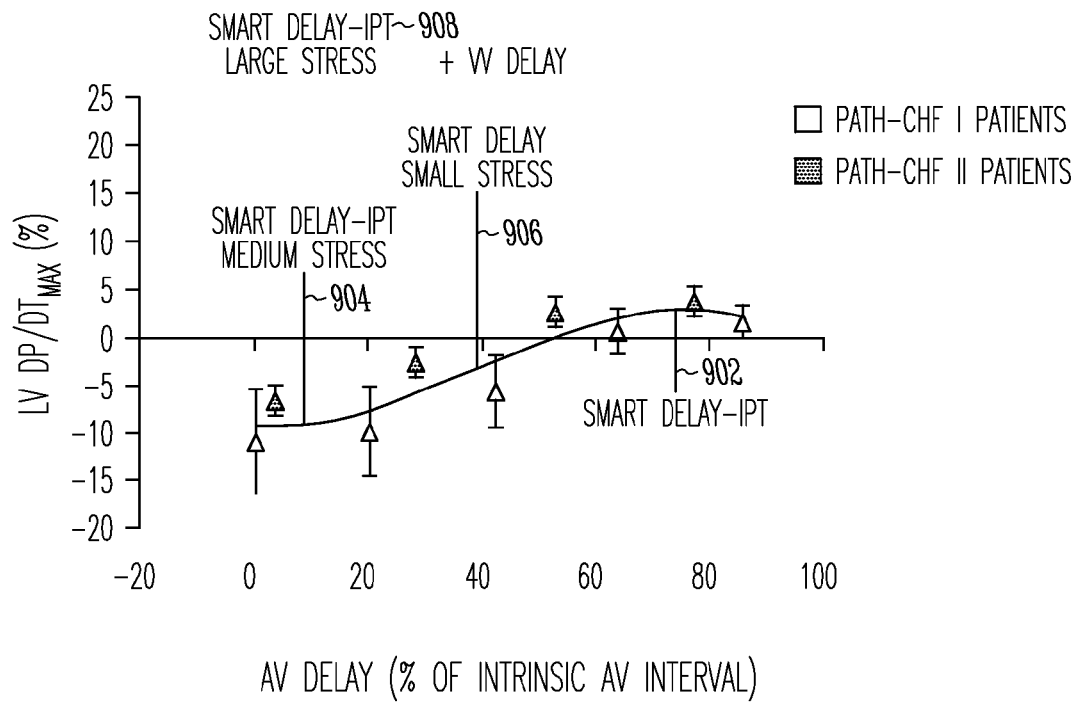

FIG. 9 illustrates an embodiment where various AV delays are recommended for CPPT for a given patient having a relatively narrow QRS, based on the amount of stress desired in the delivered CPPT. In the depicted embodiment, the SmartDelay method calculates an AV delay 902 for optimal output. A percentage of the calculated AV delay is selected using the SmartDelay-IPT method to provide a limit for CPPT. In an embodiment, a relatively small amount of stress (as delivered by the CPPT) is desired, and a medium AV delay 906 is selected, that is 40-50% of the AV interval. In one embodiment, a relatively medium amount of stress is desired, and a short AV delay 904 is selected, that is 10-20% of the AV interval. A relatively large amount of stress is desired in an embodiment 908, and a short AV delay with an additional VV delay is selected. According to various embodiments, a particular stress level is selected for each duration of CPPT delivered, and can be re-selected via the device controller or via user input (medical professional) for further therapy. In addition, the parameters can be adjusted using a closed loop system based on sensed heart-related parameters, such as heart rate (HR) in an embodiment.

Intermittent stress with pacing when introduced will likely elicit a compensatory change in HR. For example, cardiac output can drop up to 25 percent during short AV delay pacing, and HR will increase to compensate. According to various embodiments, the disclosed SmartDelay-IPT method incorporates a dynamic AV delay feature to compensate for the change in HR. In various embodiments, AV delay for CPPT will decrease with increasing HR according to programmable levels. According to one embodiment, AV delay is decreased by 10 msec for each 10 beats per minute (bpm) in an approximately linear function.

Figure 10:
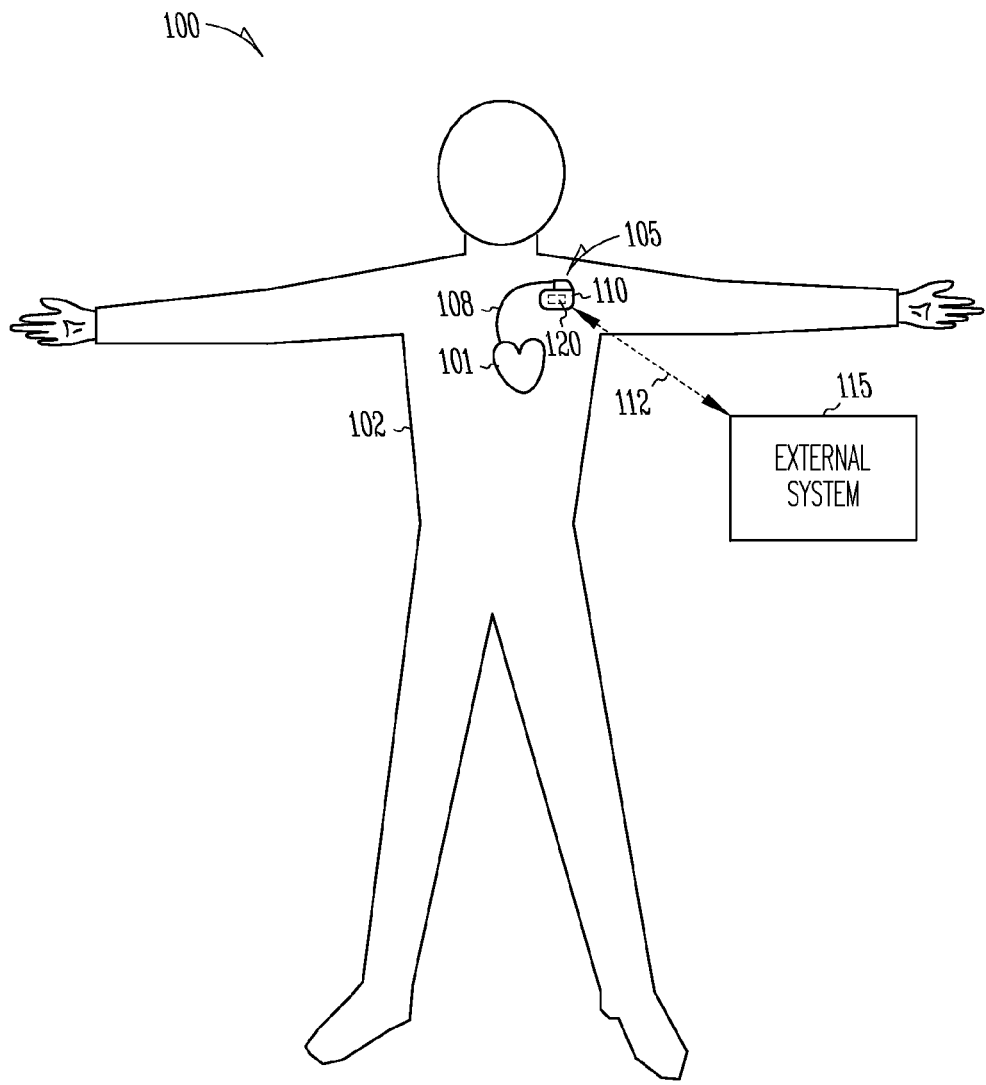
FIG. 10 is an illustration of an embodiment of a cardiac rhythm management (CRM) system including an implantable system and an external system and portions of an environment in which the CRM system is used.

FIG. 10 is an illustration of an embodiment of a cardiac rhythm management (CRM) system 100 and portions of an environment in which system 100 is used. System 100 includes an implantable system 105, an external system 115, and a telemetry link 112 providing for communication between implantable system 105 and external system 115.

Implantable system 105 includes, among other things, implantable medical device 110 and lead system 108. In various embodiments, implantable medical device 110 is an implantable CRM device including one or more of a pacemaker, a cardioverter/defibrillator, a cardiac resynchronization therapy (CRT) device, a cardiac remodeling control therapy (RCT) device, a neurostimulator, a drug delivery device or a drug delivery controller, and a biological therapy device. As illustrated in FIG. 1, implantable medical device 110 is implanted in a body 102. In various embodiments, lead system 108 includes leads for sensing physiological signals and delivering pacing pulses, cardioversion/defibrillation shocks, neurostimulation pulses, pharmaceutical agents, biological agents, and/or other types of energy or substance for treating cardiac disorders. In one embodiment, lead system 108 includes one or more pacing-sensing leads each including at least one electrode placed in or on a heart 101 for sensing electrogram and/or delivering pacing pulses. In other embodiments, electrodes placed in body 102 but away from heart 101 are used to sense physiological signals and deliver pacing pulses, cardioversion/defibrillation shocks, neurostimulation pulses, pharmaceutical agents, biological agents, and/or other types of energy or substance for treating cardiac disorders. In a specific embodiment, one or more electrodes are incorporated onto implantable medical device 110 for subcutaneous placement.

Implantable medical device 110 includes a cardiac pacing system 120. Cardiac pacing system 120 is capable of delivering cardiac protection pacing therapies (CPPT) through lead system 108. The delivery of a cardiac protection pacing therapy is timed as a cardiac protection pacing sequence including alternating pacing and non-pacing periods. In one embodiment, in addition to the cardiac protection pacing therapy, cardiac pacing system 120 also delivers one or more other cardiac pacing therapies, such as a bradycardia pacing therapy, CRT, and RCT. If another pacing therapy is being delivered when a cardiac protection pacing sequence is to be initiated, that pacing therapy is temporarily suspended to allow the delivery of the cardiac protection pacing therapy and resumed upon completion of the cardiac protection pacing sequence.

External system 115 allows a user such as a physician or other caregiver or a patient to control the operation of implantable medical device 110 and obtain information acquired by implantable medical device 110. In one embodiment, external system 115 includes a programmer communicating with implantable medical device 110 bi-directionally via telemetry link 112. In another embodiment, external system 115 is a patient management system including an external device communicating with a remote device through a telecommunication network. The external device is within the vicinity of implantable medical device 110 and communicates with implantable medical device 110 bi-directionally via telemetry link 112. The remote device allows the user to monitor and treat a patient from a distant location. The patient monitoring system is further discussed below, with reference to FIG. 13.

Telemetry link 112 provides for data transmission from implantable medical device 110 to external system 115. This includes, for example, transmitting real-time physiological data acquired by implantable medical device 110, extracting physiological data acquired by and stored in implantable medical device 110, extracting therapy history data stored in implantable medical device 110, and extracting data indicating an operational status of implantable medical device 110 (e.g., battery status and lead impedance). Telemetry link 112 also provides for data transmission from external system 115 to implantable medical device 110. This includes, for example, programming implantable medical device 110 to acquire physiological data, programming implantable medical device 110 to perform at least one self-diagnostic test (such as for a device operational status), and programming implantable medical device 110 to deliver at least one therapy.

Figure 11:
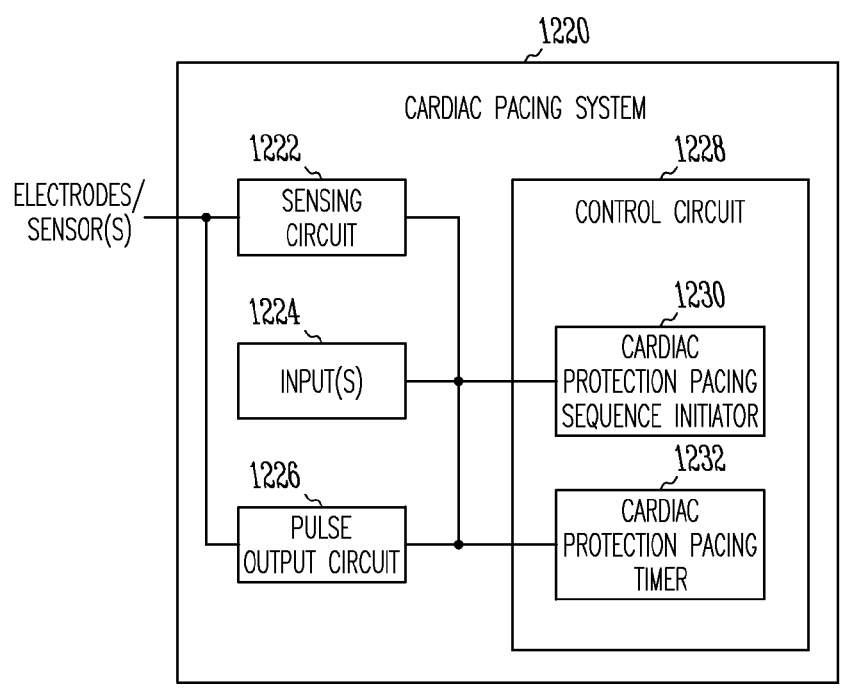
FIG. 11 is a block diagram illustrating an embodiment of portions of the circuit of a cardiac pacing system of the implantable system.

FIG. 11 is a block diagram illustrating an embodiment of portions of the circuit of a cardiac pacing system 1220. Cardiac pacing system 1220 is a specific embodiment of cardiac pacing system 120 and includes a sensing circuit 1222, SmartDelay-IPT input(s) 1224, a pulse output circuit 1226, and a control circuit 1228. Sensing circuit 1222 senses one or more signals using a plurality of electrodes and/or one or more sensors. The one or more signals are indicative of cardiac parameters. SmartDelay-IPT input(s) 1224 provide information regarding intrinsic AV intervals, interventricular (VV) timing, QRS width and LV lead/electrode location from the one or more signals and/or inputs. Pulse output circuit 1226 delivers pacing pulses to heart 101. Control circuit 1228 controls the delivery of the pacing pulses based on the one or more sensed signals and/or based on the one or more Smart-Delay-IPT inputs. In various embodiments, cardiac pacing system 1220 is substantially contained in an implantable housing of implantable medical device 110.

Control circuit 1228 includes a cardiac protection pacing sequence initiator 1230 and a cardiac protection pacing timer 1232. Cardiac protection pacing sequence initiator 1230 initiates one or more cardiac protection pacing sequences using parameters recommended based on the SmartDelay-IPT input(s). The one or more cardiac protection pacing sequences each include alternating pacing and non-pacing periods. The pacing periods each have a pacing duration during which a plurality of pacing pulse is delivered. The non-pacing periods each have a non-pacing duration during which no pacing pulse is delivered. Once a cardiac protection pacing sequence is initiated, cardiac protection pacing timer 1232 times that sequence.

Figure 12:
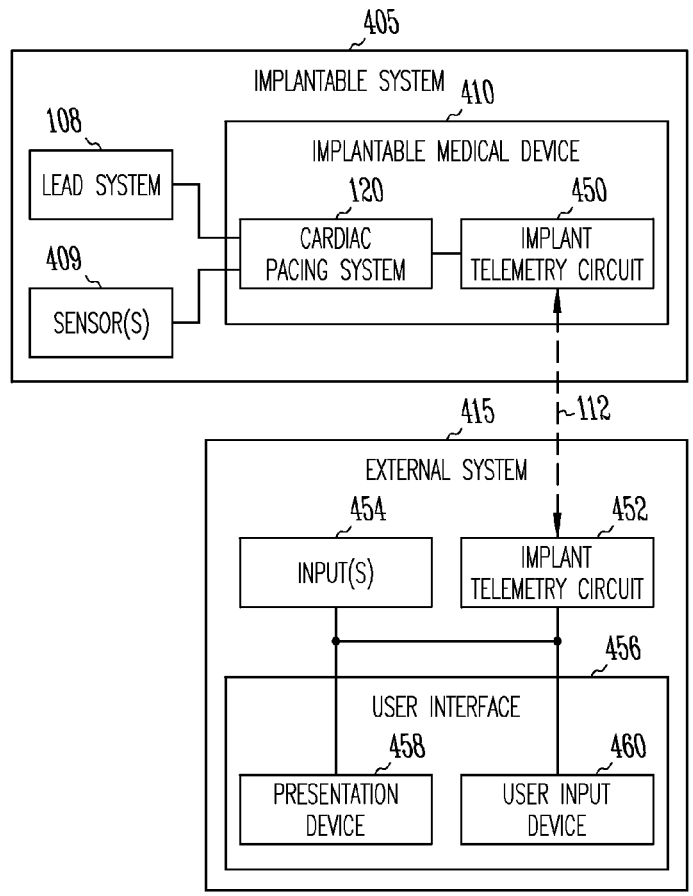
FIG. 12 is a block diagram illustrating an embodiment of portions of circuits of the implantable system and the external system.

FIG. 12 is a block diagram illustrating an embodiment of portions of circuits of an implantable system 405 and an external system 415. Implantable system 405 is a specific embodiment of implantable system 105. External system 415 is a specific embodiment of external system 115.

Implantable system 405 includes lead system 108, one or more sensors 409, and implantable medical device 410. Sensor(s) 409 includes electrodes, accelerometer(s), pressure sensor(s), and/or other sensors for sensing one or more signals required for the operation of implantable medical device 410, including detection of SmartDelay-IPT input(s). In various embodiments, sensor(s) 409 are included in an implantable housing of implantable medical device 410, attached to implantable medical device 410, coupled to implantable medical device 410 through wired or wireless connections, and/or incorporated into lead system 108. Implantable medical device 410 is a specific embodiment of implantable medical device 110 and includes cardiac pacing system 120 (including its various embodiments) and an implant telemetry circuit 450.

External system 415 includes an external telemetry circuit 452, a SmartDelay-IPT input(s) receiver 454, and a user interface 456. External telemetry circuit 452 and implant telemetry circuit 450 supports telemetry link 112, through which directional communication is performed between external system 415 and implantable system 405. User interface 456 includes a presentation device 458 and a user input device 460. Presentation device 458 includes a display screen. In one embodiment, presentation device 458 further includes a printer and a speaker. User input device 460 allows programming of implantable medical device 410, including the entry of commands for initiating one or more cardiac protection pacing sequences and/or parameters controlling the delivery of the cardiac protection pacing therapy. In one embodiment, portions of presentation device 458 and user input device 460 are integrated as an interactive screen. SmartDelay-IPT input(s) receiver 454 receives sensed data regarding, for example, sensed intrinsic timing, lead/electrode location and AV intervals, via telemetry from the implantable system, according to various embodiments. In various embodiments, SmartDelay-IPT input(s) may be entered by a user, such as a medical professional, using user input device 460. In one embodiment, external system 415 includes a programmer. In another embodiment, external system 415 includes a patient management system as discussed below with reference to FIG. 13.

Figure 13:
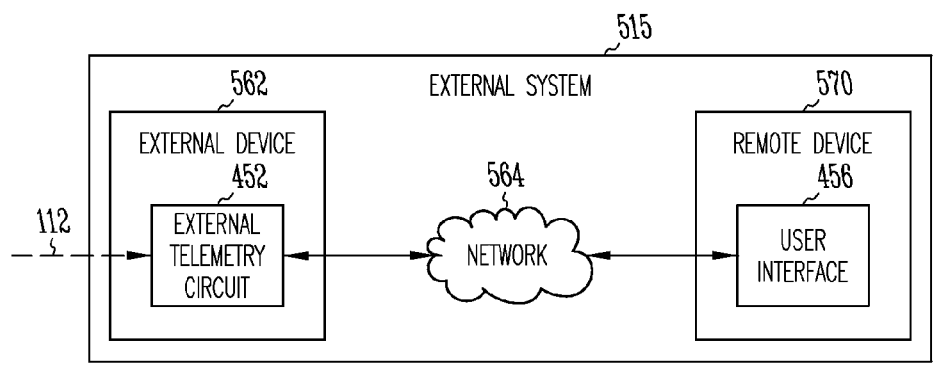
FIG. 13 is a block diagram illustrating an embodiment of the external system.

FIG. 13 is a block diagram illustrating an embodiment of an external system 515, which is a specific embodiment of external system 415. As illustrated in FIG. 5, external system 515 is a patient management system including an external device 562, a telecommunication network 564, and a remote device 570. External device 562 is placed within the vicinity of an implantable medical device and includes external telemetry system 452 to communicate with the implantable medical device via telemetry link 112. Remote device 570 is in one or more remote locations and communicates with external device 562 through network 564, thus allowing a physician or other caregiver to monitor and treat a patient from a distant location and/or allowing access to various treatment resources from the one or more remote locations. In one embodiment, as illustrated in FIG. 5, remote device 570 includes user interface 456. This allows the user to initiate and/or adjust the cardiac protection pacing.

Figure 14:
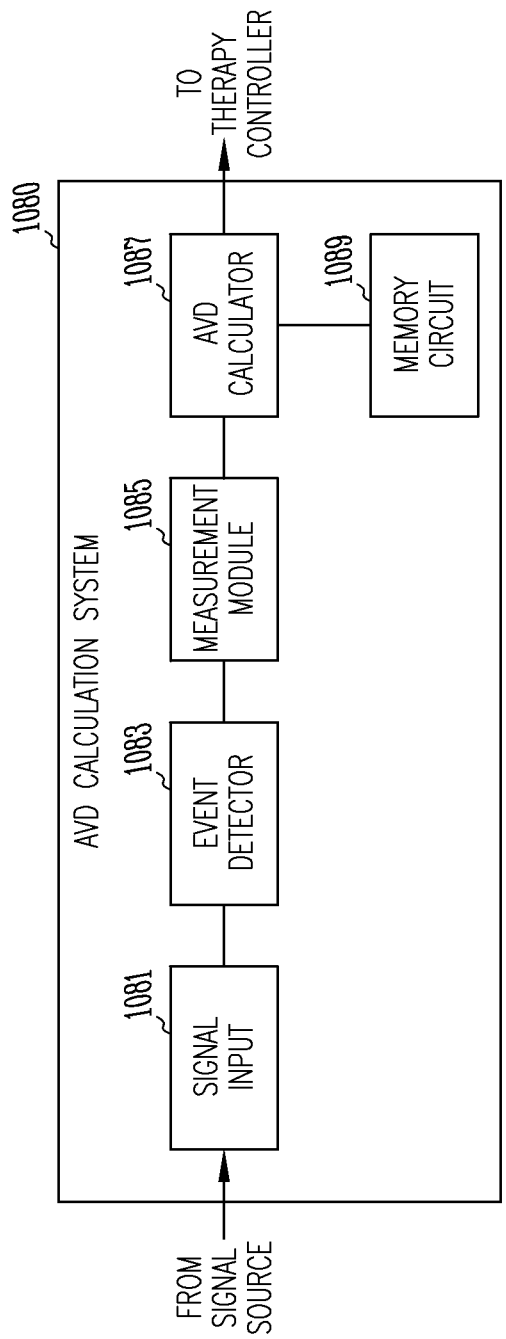
FIG. 14 is a block diagram illustrating an embodiment of a system for calculating atrioventricular (AV) delay.

FIG. 14 is a block diagram illustrating a system 1080 for calculating AV delay (AVD) using one or more of the methods discussed above. System 1080 includes a signal input 1081, an event detector 1083, a measurement module 1085, an AVD calculator 1087, and a memory circuit 1089. In one embodiment, system 1080 is included in implantable system 405. In another embodiment, system 1080 is included in external system 415, such as a programmer. In yet another embodiment, portions of system 1080 are included in implantable system 405 and external system 415.

In one embodiment, signal input 1081 includes a cardiac signal input that receives the one or more of the cardiac signals sensed by sensor 409. In one embodiment, signal input 1081 further includes a mechanical signal input. Event detector 1083 detects the events required for AVD calculation. Measurement module 1085 measures time intervals between two of these events. In one embodiment, measurement module 1085 measures one or more of post-sensing time intervals. AVD calculator 1087 then calculates one or more post-sensing AVD time intervals based on the one or more of the post-sensing time intervals according to the formulas presented above. According to various embodiments, the AVD calculator is adapted to calculate an AVD using the AV interval and a predetermined equation relating the AV interval to an optimal AVD to provide a maximum positive rate of left ventricular pressure change during systole, LV+dp/dt, and further to calculate a percentage of the optimal AVD to deliver ventricular pacing pulses to provide a desired level of stress for cardiac protective pacing therapy (CPPT) to provide a cardiac conditioning therapy to improve autonomic balance. According to various embodiments, the system further includes inputs for one or more of intrinsic interventricular timing, left ventricular (LV) lead/electrode location, QRS width, and heart rate (HR). AVD is calculated using one or more of intrinsic interventricular timing, left ventricular (LV) lead/electrode location, QRS width, and heart rate (HR), in various embodiments.

In one embodiment, memory circuit 1089 contains all the coefficients of the formulas used for the calculation of the AVD time intervals. In one embodiment, the coefficients are programmable. The user may enter new coefficients to replace the coefficients stored in memory circuit 1089. In one embodiment, the calculated AVD time intervals are also stored in memory circuit 1089. After at least one new AVD time interval is calculated, AVD calculator 1087 sends the new AVD time interval to the therapy timing controller of implantable device 410 to control the timing of deliveries of ventricular pacing pulses.

One of ordinary skill in the art will understand that, the modules and other circuitry shown and described herein can be implemented using software, hardware, and combinations of software and hardware. As such, the terms module and circuitry, for example, are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a computer data signal embodied in a carrier wave or propagated signal, that represents a sequence of instructions which, when executed by one or more processors cause the processor(s) to perform the respective method. In various embodiments, the methods are implemented as a set of instructions contained on a computer-accessible medium capable of directing a processor to perform the respective method. In various embodiments, the medium is a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for delivering pacing pulses, comprising:
sensing intrinsic atrioventricular (AV) intervals;
using the intrinsic AV interval and a predetermined equation relating the AV interval to a calculated optimal AV delay to provide a maximum positive rate of left ventricular pressure change during systole; and calculating an AV delay using a predetermined percentage of the calculated optimal AV delay to deliver ventricular pacing pulses, wherein the predetermined percentage is less than 100%, to provide a desired level of stress by introducing or augmenting dyssynchrony for cardiac protective pacing therapy (CPPT) to provide a cardiac conditioning therapy to improve autonomic balance.

2. The method of claim 1, further comprising:
receiving LV electrode location; and
calculating the AV delay using the LV electrode location.

3. The method of claim 1, further comprising:
sensing intrinsic interventricular (VV) interval; and
calculating the AV delay using the sensed intrinsic VV interval.

4. The method of claim 1, further comprising:
sensing QRS width; and
calculating the AV delay using the sensed QRS width.

5. The method of claim 4, wherein calculating the AV delay includes calculating a first AV delay for a wide QRS width and a second AV delay for a narrow QRS width.

6. The method of claim 5, wherein a wide QRS width includes QRS width greater than approximately 150 msec.

7. The method of claim 5, wherein a narrow QRS width includes QRS width greater than approximately 120 msec and less then approximately 150 msec.

8. The method of claim 1, further comprising:
sensing heart rate (HR) in response to the pacing sequences;
dynamically adjusting parameters of the AV delay for the CPPT based on the sensed HR.

9. A method for operating a cardiac pacing device, comprising:
delivering cardiac protective pacing therapy (CPPT) to provide a cardiac conditioning therapy to improve autonomic balance to one or more ventricular sites in an atrial tracking pacing mode with an atrioventricular (AV) delay;
sensing intrinsic AV intervals;
modulating the AV delay based on the sensed intrinsic AV intervals, including calculating AV delay using the intrinsic AV interval and a predetermined equation relating the AV interval to a calculated optimal AV delay, and using a predetermined percentage of the calculated optimal AV delay to deliver ventricular pacing pulses to provide a desired level of stress by introducing or augmenting dyssynchrony for the CPPT, wherein the predetermined percentage is less than 100%;
sensing heart rate (HR) in response to the pacing pulses; and
dynamically adjusting parameters of the AV delay for the pacing pulses based on the sensed HR in a closed loop system.

10. The method of claim 9, further comprising:
receiving LV electrode location; and
modulating the AV delay using the LV electrode location.

11. The method of claim 9, further comprising:
sensing intrinsic interventricular (VV) interval; and
modulating the AV delay using the sensed intrinsic VV interval.

12. The method of claim 9, further comprising:
sensing QRS width; and
modulating the AV delay using the sensed QRS width.

13. The method of claim 9, wherein modulating AV delay includes using a short AV delay to provide a first selected amount of stress during cardioprotective pacing.

14. The method of claim 13, wherein using a short AV delay includes using an AV delay that is 10 to 20 percent of the intrinsic AV interval.

15. The method of claim 13, wherein modulating AV delay includes using a long AV delay to provide a second selected amount of stress during cardioprotective pacing, wherein the second amount is greater than the first amount.

16. The method of claim 15, wherein using a long AV delay includes using an AV delay that is 80 to 95 percent of the intrinsic AV interval.

17. The method of claim 15, wherein modulating AV delay includes using an AV delay and a VV delay to provide a third selected amount of stress during cardioprotective pacing, wherein the third amount is greater than the second amount.

18. A system, comprising:
a signal input to receive at least one cardiac signal indicative of cardiac events including at least one atrial event and one ventricular event;
an event detector, coupled to the signal input, to detect the at least one atrial event and one ventricular event;
a measurement module, coupled to the event detector, to measure an atrioventricular (AV) time interval between an atrial event and a ventricular event; and
an AV delay calculator coupled to the measurement module, the AV delay calculator adapted to calculate an AV delay using the AV interval and a predetermined equation relating the AV interval to a calculated optimal AV delay to provide a maximum positive rate of left ventricular pressure change during systole, and further adapted to calculate a percentage of the calculated optimal AV delay to deliver ventricular pacing pulses to provide a desired level of stress by introducing or augmenting dyssynchrony for cardiac protective pacing therapy (CPPT) to provide a cardiac conditioning therapy to improve autonomic balance, wherein the percentage is less than 100%.

19. The system of claim 18, further comprising an input for sensing intrinsic interventricular timing.

20. The system of claim 18, further comprising an input for receiving left ventricular (LV) lead location.

21. The system of claim 18, further comprising an input for sensing QRS width.

22. The system of claim 18, further comprising an input for sensing heart rate (HR).

* * * * *